United States Patent
Hara et al.

(10) Patent No.: US 10,214,754 B2
(45) Date of Patent: Feb. 26, 2019

(54) TRANSFORMANT AND ITS PRODUCTION PROCESS, AND METHOD FOR PRODUCING LACTIC ACID

(71) Applicant: JMTC Enzyme Corporation, Tokyo (JP)

(72) Inventors: Futoshi Hara, Yokohama (JP); Ayako Kashima, Yokohama (JP); Shuichiro Kimura, Kanonji (JP)

(73) Assignee: JMTC Enzyme Corporation, Tokyo (JP)

( * ) Notice: Subject to any disclaimer, the term of this patent is extended or adjusted under 35 U.S.C. 154(b) by 0 days.

(21) Appl. No.: 15/506,960

(22) PCT Filed: Oct. 6, 2015

(86) PCT No.: PCT/JP2015/078394
§ 371 (c)(1),
(2) Date: Feb. 27, 2017

(87) PCT Pub. No.: WO2016/056566
PCT Pub. Date: Apr. 14, 2016

(65) Prior Publication Data
US 2017/0356017 A1 Dec. 14, 2017

(30) Foreign Application Priority Data
Oct. 10, 2014 (JP) .................................. 2014-209048

(51) Int. Cl.
| C12N 1/14 | (2006.01) |
| C12P 7/56 | (2006.01) |
| C12R 1/645 | (2006.01) |
| C12N 15/52 | (2006.01) |
| C12N 9/04 | (2006.01) |
| C12N 9/88 | (2006.01) |

(52) U.S. Cl.
CPC ............... *C12P 7/56* (2013.01); *C12N 9/0006* (2013.01); *C12N 9/88* (2013.01); *C12N 15/52* (2013.01); *C12R 1/645* (2013.01); *C12Y 101/01027* (2013.01); *C12Y 401/01001* (2013.01)

(58) Field of Classification Search
CPC ........ C12P 7/56; C12N 15/815; C12N 9/0006
USPC ............... 435/139, 190, 254.2, 471
See application file for complete search history.

(56) References Cited

U.S. PATENT DOCUMENTS

| 9,284,561 B2* | 3/2016 | Hara ..................... C12N 9/0006 |
| 9,428,777 B2* | 8/2016 | Hara ....................... C12N 1/16 |
| 2003/0166179 A1* | 9/2003 | Rajgarhia ............ C12N 9/0006 435/139 |
| 2003/0228671 A1 | 12/2003 | Hause et al. | |
| 2012/0214214 A1* | 8/2012 | Hara ..................... C12N 9/0006 435/139 |
| 2015/0044740 A1 | 2/2015 | Kim et al. | |
| 2015/0232895 A1 | 8/2015 | Hara et al. | |

FOREIGN PATENT DOCUMENTS

| EP | 1975232 A1 | 10/2008 |
| JP | 2003505065 A | 2/2003 |
| JP | 2003274958 A | 9/2003 |
| JP | 2003535583 A | 12/2003 |
| JP | 2007512018 A | 5/2007 |
| JP | 2007530007 A | 11/2007 |
| JP | 2008092862 A | 4/2008 |
| JP | 2009537144 A | 10/2009 |
| WO | 2011021629 A1 | 2/2011 |
| WO | 2012074818 A2 | 6/2012 |
| WO | 2014030655 A1 | 2/2014 |

OTHER PUBLICATIONS

Branduardi Paola et al: "Lactate production yield from engineered yeasts is dependent from the host background, the lactate dehydrogenase source and the lactate export", Microbial Cell Factories, vol. 5, No. 1, Jan. 30, 2006 (Jan. 30, 2006), p. 4, XP021017792, ISSN: 1475-2859, DOI: 10.1186/1475-2859-5-4.
Bauer M et al: "16 Years research on lactic acid production with yeast—Ready for the market?", Biotechnology and Genetic Engineering Rev, Intercept Ltd., Andover, GB, vol. 27, Jan. 1, 2010 (Jan. 1, 2010), pp. 229-256, XP009181318, ISSN: 0264-8725, DOI: 10.1080/02648725.2010.10648152.
European Patent Office, Seach Report issued in European Patent Application No. 15849633.1 dated Mar. 13, 2018, 9 pages.
Futoshi Hara et al., "Lactate production using Schizosaccharomyces Pombe," 2009, The 61st Abstracts of the Annual Meeting of the Society for Biotechnology, Japan, p. 190, 2Mp08.
PCT Office, International Search Report issued in corresponding PCT Application No. PCT/JP2015/078394 dated Dec. 1, 2015, 4 pages.
Akada et al, Sets of Integrating Plasmids and Gene Disruption Cassettes Containing Improved Counter-Selection Markers Designed for Repeated Use in Budding, Yeast, 2002, vol. 19, p. 393-402.
Japanese Patent Office, Office Action issued in JP 2014-236022 dated Jun. 19, 2018, 9 pages.
Arndt, GM, et al., Gene regulation by antisense RNA in the fission yeast Schizosaccharomyces pombe, Mol Gen Genet, 1995, 248 (3), 293-300.
P40370 ver 110, UniProt/Swiss-Prot, Nov. 13, 2013, Schizosaccharomyces pombe (strain 972/ATCC 24843) gene eno101.

(Continued)

*Primary Examiner* — Tekchand Saidha
(74) *Attorney, Agent, or Firm* — Wood Herron & Evans LLP

(57) ABSTRACT

Provided is a transformant which can produce lactic acid with a high productivity without requiring neutralization with an alkali and is excellent in both of lactic acid production capability and growth ability and its production process, and a method for producing lactic acid by using the transformant. A transformant comprising 3 copies of a human lactate dehydrogenase gene that is introduced into a *Schizosaccharomyces pombe* host, wherein a gene encoding pyruvate decarboxylase 2 of the *Schizosaccharomyces pombe* host is deleted or inactivated.

10 Claims, 3 Drawing Sheets
Specification includes a Sequence Listing.

(56) References Cited

OTHER PUBLICATIONS

Q8NKC2 ver 83, UniProt/Swiss-Prot, Nov. 13, 2013, Schizosaccharomyces pombe (strain 972/ATCC 24843) gene eno102.
P36580 ver 98, UniProt/Swiss-Prot, Nov. 13, 2013, Schizosaccharomyces pombe (strain 972/ATCC 24843) gene fba1.
O43026 ver 106, UniProt/Swiss-Prot, Nov. 13, 2013, Schizosaccharomyces pombe (strain 972/ATCC 24843) gene gpd3.
P36623 ver 122, UniProt/Swiss-Prot, Nov. 13, 2013, Schizosaccharomyces pombe (strain 972/ATCC 24843) gene gpm1.
P09988 ver 124, UniProt/Swiss-Prot, Nov. 13, 2013, Schizosaccharomyces pombe (strain 972/ATCC 24843) gene hht2.
O60101 ver 94, UniProt/Swiss-Prot, Nov. 13, 2013, Schizosaccharomyces pombe (strain 972/ATCC 24843) gene pgk1.
P07669 ver 113, UniProt/Swiss-Prot, Nov. 13, 2013, Schizosaccharomyces pombe (strain 972/ATCC 24843) gene tpi1.
P0CG72 ver 23, UniProt/Swiss-Prot, Nov. 13, 2013, Schizosaccharomyces pombe (strain 972/ATCC 24843) gene ubi4.
P78958 ver 113, UniProt/Swiss-Prot, Nov. 13, 2013, Schizosaccharomyces pombe (strain 972/ATCC 24843) gene gpd1.
Japanese Patent Office, Office Action issued in JP 2014-236021 dated Aug. 7, 2018, 10 pages.

* cited by examiner pSM-HsLDH vector
4562 bp pSM-HsLDH vector
4535 bp

TRANSFORMANT AND ITS PRODUCTION PROCESS, AND METHOD FOR PRODUCING LACTIC ACID

TECHNICAL FIELD

The present invention relates to a transformant and its production process, and a method for producing lactic acid. Specifically, a transformant containing a lactate dehydrogenase gene (a gene encoding lactate dehydrogenase (LDH), and hereinafter also referred to as LDH gene) introduced into *Schizosaccharomyces pombe* (hereinafter also referred to as *S. pombe*), wherein a gene that is a part of a group of genes encoding pyruvate decarboxylase is deleted or inactivated, a production process of the transformant, and a method for producing lactic acid by cultivating the transformant in a culture broth and recovering lactic acid from the culture broth.

BACKGROUND ART

Lactic acid is widely used in food and chemical raw materials used for medicine, cosmetics, etc. Further, polylactic acid obtained by using lactic acid has attracted attention as a biodegradable plastic which is degraded finally to carbon dioxide and water by microorganisms. Therefore, it is necessary to produce lactic acid at a low cost with a high productivity.

As a method for producing lactic acid, a biological production method in which a saccharide is fermented by lactic acid bacteria. However, since the acid resistance of lactic acid is low, in order to achieve a high productivity of this method, the lactic acid produced by fermentation is required to be converted into a lactic acid salt by neutralizing it with an alkali. Such neutralization with an alkali requires a step for restoring lactic acid from the lactic acid salt, whereby the production steps become complicated and the production cost becomes high.

As a method for obtaining lactic acid without carrying out neutralization with an alkali, a method which uses a transformant prepared by introducing a gene encoding LDH into a yeast host. For example, Patent Document 1 discloses that lactic acid can be produced with a high productivity, without carrying out a neutralization step with an alkali, by cultivating a transformant containing an LDH gene which is derived from mammals such as human and is introduced into a *S. pombe* host, wherein a gene that is a part of a group of genes encoding pyruvate decarboxylase of the *S. pombe* host is deleted or inactivated. Further, Patent Document 2 discloses that lactic acid can be obtained by using a transformant prepared by introducing an L-lactate dehydrogenase gene of *Lactobacillus plantarum* into a *Saccharomyces cerevisiae* that does not essentially produce ethanol when it is cultured in a culture medium.

Further, Patent Document 3 discloses that a transformant containing an LDH gene of *Lactobacillus pentosus* (LpLDH gene) introduced into a *S. pombe* host, wherein a gene that is a part of a group of genes encoding pyruvate decarboxylase of the *S. pombe* host is deleted or inactivated, has a lactic acid production capability at the same level as or a greater level than the transformant described in Patent Document 1. And particularly, it discloses that, by introducing an LpLDH gene in combination with a LDH gene derived from human (HsLDH gene), the lactic acid production capability can be improved significantly as compared with a transformant transformed with a single copy of HsLDH gene or a transformant transformed with a single copy of HsLDH gene and a single copy of a LDH gene derived from other species.

CITATION LIST

Patent Literature

[Patent Document 1] PCT International Publication No. WO2011/021629

[Patent Document 2] Published Japanese Translation No. 2007-512018 of the PCT International Publication

[Patent Document 3] PCT International Publication No. WO2014/030655

SUMMARY OF INVENTION

Technical Problem

To produce lactic acid efficiently, a transformant excellent in both of lactic acid production capability and growth ability is preferred. However, as described in the following Example 1, it is general tendency of a mutant strain prepared by introducing a foreign LDH gene that one having a high lactic acid production capability shows a low growth ability.

The present invention is to provide a *S. pombe* transformant which can produce lactic acid with a high productivity without requiring neutralization with an alkali and is excellent in both of lactic acid production capability and growth ability, and production process thereof.

Further, the present invention is to provide a method for producing lactic acid, with a high productivity without requiring neutralization with an alkali, by using the transformant.

Here, the lactic acid according to the present invention means L-lactic acid which is obtained by a biological method.

Solution to Problem

The first embodiment of the present invention is a transformant containing from 3 to 5 copies of a lactate dehydrogenase gene derived from human and introduced into a *Schizosaccharomyces pombe* host, wherein a gene that is a part of a group of genes encoding pyruvate decarboxylase of the *Schizosaccharomyces pombe* host is deleted or inactivated.

Further, the second embodiment of the present invention is a transformant characterized by providing a cell concentration of at least 4.0 g (on a dry cell weight basis)/L of a culture broth prepared by inoculating cells, at an initial cell concentration of 0.04 g (on a dry cell weight basis)/L, into a 500 mL Sakaguchi flask containing 100 mL of a liquid culture broth which includes 1% of yeast extract, 2% of peptone and 6% of glucose, and then cultivating 20 hours at a temperature of 32° C. under shaking conditions of 110 rpm and 7 cm stroke, and providing a lactic acid concentration of at least 80 g/L of a fermentation liquor prepared by inoculating cells, at an initial cell concentration of 0.04 g (on a dry cell weight basis)/L, into a 500 mL Sakaguchi flask containing 100 mL of a liquid culture broth which includes 1% of yeast extract, 2% of peptone and 6% of glucose, and then cultivating 20 hours at a temperature of 32° C. under shaking conditions of 110 rpm and 7 cm stroke, followed by inoculating thus obtained cells, at an initial cell concentration of 36 g (on a dry cell weight basis)/L, into a test tube having a diameter of 18 mm and a length of 150 mm and containing 4.5 mL of a 11.1% glucose aqueous solution, and then fermenting 3 hours at a temperature of 32° C. under shaking conditions of 43.5° shaking angle, 110 rpm and 7 cm stroke.

The transformant is preferably a transformant containing at least one lactate dehydrogenase gene introduced into a *Schizosaccharomyces pombe* host, wherein a gene that is a part of a group of genes encoding pyruvate decarboxylase of the *Schizosaccharomyces pombe* host is deleted or inactivated.

In both the first embodiment and the second embodiment of the present invention, the deleted or inactivated gene encoding pyruvate decarboxylase is preferably a PDC2 gene. Further, the LDH gene is preferably integrated into *Schizosaccharomyces pombe* chromosome.

Further, the process for producing the transformant of the present invention is a process for producing a transformant containing from 3 to 5 copies of a lactate dehydrogenase gene derived from human and having deletion or inactivation of a gene that is a part of a group of genes encoding pyruvate decarboxylase, characterized by introducing an expression cassette that comprises a promoter and a terminator capable of functioning in *Schizosaccharomyces pombe* and a lactate dehydrogenase gene into from 3 to 5 positions of chromosome of a *Schizosaccharomyces pombe* host to obtain a transformant, and using a host in which a gene that is a part of a group of genes encoding pyruvate decarboxylase is deleted or inactivated as the *Schizosaccharomyces pombe* host or deleting or inactivating a gene that is a part of a group of genes encoding pyruvate decarboxylase of the obtained transformant.

In the process for producing the transformant of the present invention, the expression cassette is preferably introduced into a region selected from a region that comprises from 10,000 bp upstream to 10,000 bp downstream of an eno101 gene locus, a region that comprises from 10,000 bp upstream to 10,000 bp downstream of a leu1 gene locus, and a region that comprises from 10,000 bp upstream to 10,000 bp downstream of a gpm1 gene locus.

Further, in the process for producing the transformant of the present invention, the deleted or inactivated gene encoding pyruvate decarboxylase is preferably a PDC2 gene.

Further, the method for producing lactic acid of the present invention is comprised of cultivating the transformant, and recovering lactic acid from a culture broth.

In the method for producing lactic acid of the present invention, a culture broth having a glucose concentration of from 1 to 50 mass % is preferably used for cultivating the transformant. Further, the cultivating is preferably continued after pH of the culture broth becomes 3.5 or lower due to the lactic acid produced by the transformant.

Further, the cultivating is preferably continued without neutralizing the lactic acid produced by the transformant in the culture broth, and lactic acid is preferably separated from the culture broth without neutralizing the lactic acid produced by the transformant in the culture broth.

Advantageous Effects of Invention

The *S. pombe* transformant of the present invention is excellent in growth ability, and can produce lactic acid with a high productivity without requiring neutralization with an alkali. Further, it is suitable for the production of lactic acid in the presence of high concentration of saccharides, particularly glucose, fructose, sucrose and maltose, and is also suitable for a high density cultivation. Further, it is also excellent in a long-term lactic acid production capability in a continuous culture under high oxygen conditions.

The transformant can be produced conveniently, according to the transformant production process of the present invention.

Further, the lactic acid production method of the present invention can produce lactic acid with a high productivity without carrying out a neutralization step with an alkali.

DESCRIPTION OF EMBODIMENTS

[Transformant]

Figure 1:
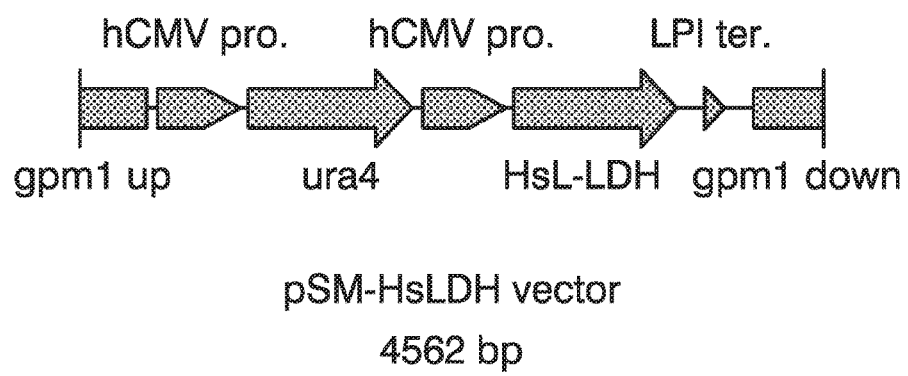
FIG. 1 is a schematic figure illustrating the structure of recombinant vector pSM-HsLDH vector.

The transformant of the first embodiment of the present invention is characterized by containing from 3 to 5 copies of a lactate dehydrogenase gene derived from human and introduced into a *Schizosaccharomyces pombe* host, wherein a gene that is a part of a group of genes encoding pyruvate decarboxylase of the *Schizosaccharomyces pombe* host is deleted or inactivated. The transformant of the first embodiment of the present invention has a sufficiently high growth ability, despite it has a high lactic acid production capability. Therefore, it is very suitable as a lactic acid bacterium for producing lactic acid in an industrial scale.

The deleted or inactivated gene encoding pyruvate decarboxylase is preferably a PDC2 gene. Further, the LDH gene is preferably integrated into *Schizosaccharomyces pombe* chromosome.

The transformant of the second embodiment of the present invention is characterized by providing a cell concentration of at least 4.0 g (on a dry cell weight basis)/L of a culture broth prepared by inoculating cells, at an initial cell concentration of 0.04 g (on a dry cell weight basis)/L, into a 500 mL Sakaguchi flask containing 100 mL of a liquid culture broth which includes 1% of yeast extract, 2% of peptone and 6% of glucose, and then cultivating 20 hours at a temperature of 32° C. under shaking conditions of 110 rpm and 7 cm stroke, and providing a lactic acid concentration of at least 80 g/L of a fermentation liquor prepared by inoculating cells, at an initial cell concentration of 0.04 g (on a dry cell weight basis)/L, into a 500 mL Sakaguchi flask containing 100 mL of a liquid culture broth which includes 1% of yeast extract, 2% of peptone and 6% of glucose, and then cultivating 20 hours at a temperature of 32° C. under shaking conditions of 110 rpm and 7 cm stroke, followed by inoculating thus obtained cells, at an initial cell concentration of 36 g (on a dry cell weight basis)/L, into a test tube having a diameter of 18 mm and a length of 150 mm and containing 4.5 mL of a 11.1% glucose aqueous solution, and then fermenting 3 hours at a temperature of 32° C. under shaking conditions of 43.5° shaking angle, 110 rpm and 7 cm stroke.

As described above, the transformant of the second embodiment of the present invention has a sufficiently high growth ability, despite it has a high lactic acid production capability. Therefore, it is very suitable as a lactic acid bacterium for producing lactic acid in an industrial scale.

The transformant of the second embodiment of the present invention is preferably a transformant containing an LDH gene introduced into a S. pombe host, wherein a gene that is a part of a group of genes encoding pyruvate decarboxylase of the S. pombe host is deleted or inactivated. The transformant of the first embodiment of the present invention is particularly preferred as such a transformant.

<S. pombe>

S. pombe as the host is a yeast of the genus Schizosaccharomyces (fission yeast), and is a microorganism which is particularly excellent in acid resistance as compared with other yeasts. Further, S. pombe has been known to be excellent in the productivity of lactic acid under a high concentration of glucose and is also suitable for a high density cultivation (cultivation using a large amount of yeast), in comparison with other yeasts such as Saccharomyces cerevisiae. Therefore, by using a S. pombe transformant, lactic acid can be produced with a significantly high productivity.

Here, the entire nucleotide sequence of the chromosomes of S. pombe is stored and opened to the public in the database "PomBase (http://www.pombase.org/)". The sequence data of S. pombe genes described in the present specification are available from the database by searching with a gene name or the above-mentioned systematic ID.

<Gene Encoding Pyruvate Decarboxylase>

There are 4 types of genes in the group of genes encoding pyruvate decarboxylase (pyruvate decarboxylase gene, hereinafter referred to as "PDC gene") of S. pombe, and the group is comprised of a gene encoding pyruvate decarboxylase 1 (hereinafter referred to as "PDC 1 gene"), a gene encoding pyruvate decarboxylase 2 (hereinafter referred to as "PDC 2 gene"), a gene encoding pyruvate decarboxylase 3 (hereinafter referred to as "PDC 3 gene"), and a gene encoding pyruvate decarboxylase 4 (hereinafter referred to as "PDC 4 gene"). Among them, PDC 2 gene and PDC 4 gene are the PDC genes which have major functions in S. pombe. Systematic IDs of the respective PDC genes are as follows.

PDC 1 gene (Pdc 1): SPAC13A11.06
PDC 2 gene (Pdc 2): SPAC1F8.07c
PDC 3 gene (Pdc 3): SPAC186.09
PDC 4 gene (Pdc 4): SPAC3G9.11c The sequence data of each PDC gene can be obtained from the above-described S. pombe gene database by searching with the gene names or the systematic IDs.

In the case of wild-type S. pombe, glucose is metabolized into pyruvic acid by the glycolytic pathway, the pyruvic acid is converted into acetaldehyde by the pyruvate decarboxylase expressed from the above-mentioned PDC gene, and then the acetaldehyde is converted into ethanol by an alcohol dehydrogenase, whereby ethanol fermentation is carried out. Further, since wild-type S. pombe does not have a functional LDH gene, it does not have a route for producing lactic acid from pyruvic acid.

On the other hand, the LDH expressed from the introduced LDH gene produces lactic acid by reducing pyruvic acid to lactic acid. Therefore, even when wild-type S. pombe is enabled to produce lactic acid by introducing an LDH gene thereto, its lactic acid productivity does not become sufficiently high because both of the ethanol fermentation and the lactic acid fermentation are carried out if it is as such.

The transformant of the present invention has a chromosome wherein a part of the group of genes encoding pyruvate decarboxylase is deleted or inactivated. By the deletion or inactivation of a gene that is a part of the group of PDC genes of the transformant, the ethanol fermentation efficiency decreases and the amount of pyruvic acid to be converted into ethanol decreases, whereby the productivity of lactic acid increases. However, when all the genes of the PDC gene group are deleted or inactivated, the growth is inhibited because the ethanol fermentation cannot be carried out at all. Therefore, the deletion or inactivation is limited to a part of the group of PDC genes.

It is particularly preferred that the PDC gene to be deleted or inactivated is PDC2 gene. The PDC2 gene is a PDC gene which has a particularly main function.

As described above, if all of the PDC genes are deleted or inactivated, the growth of the transformant is inhibited because it cannot carry out ethanol fermentation. Therefore, the deletion or inactivation of PDC genes should be carried out in such a manner that the fermentation efficiency of lactic acid can be increased by lowing the ethanol fermentation ability, while maintaining an ethanol fermentation ability necessary for the growth to obtain a sufficient amount of transformants. The present inventors carried out extensive studies on this issue, and as a result, have found that when PDC 2 gene is deleted or inactivated, PDC 4 gene is activated to a certain degree, whereby it becomes possible to attain both the ethanol fermentation ability for obtaining sufficient amount of the transformant and the production of lactic acid at a high fermentation efficiency.

Deletion or inactivation of PDC genes can be carried out by publicly known methods. For example, the Latour system (Nucleic Acids Res., 2006, vol. 34, page ell, and WO2007/063919) can be used to delete a PDC gene.

Further, the PDC gene may be inactivated by causing deletion, insertion, substitution or addition in a part of the nucleotide sequence of the PDC gene. The gene may be mutated by only one of the deletion, insertion, substitution and addition, or by two or more of them.

As a method for introducing the above-described mutation to a part of the PDC gene, publicly known methods can be used. For example, a mutant screening method using mutagens (Koubo Bunshi Idengaku Jikken-Hou, 1996, Japan Scientific Societies Press), random mutations using PCR (polymerase chain reaction) (PCR Methods Appl., 1992, vol. 2, p. 28-33) and the like.

Further, the PDC gene in which a mutation was introduced into a part thereof may express a temperature-sensitive mutant type pyruvate decarboxylase. The temperature-sensitive mutant type pyruvate decarboxylase is an enzyme which shows an activity equivalent to that of the wild-type pyruvate decarboxylase at a certain cultivation temperature but shows disappearance or lowering of the activity when the cultivation temperature reaches to a specific temperature or higher.

The mutant strain which expresses such a mutant type pyruvate decarboxylase can be obtained by selecting a strain showing a growth rate equivalent to that of the wild-type yeast under a temperature condition at which the activity is not limited, while showing a significant decrease in the growth rate under a specific temperature condition at which the activity is limited.

<LDH Gene>

The transformant of the present invention has at least one LDH gene. As described above, *S. pombe* essentially does not have an LDH gene showing a strong enzymatic activity. Therefore, the transformant is obtained by introducing an LDH gene of an organism other than *S. pombe* into *S. pombe* by genetic engineering methods.

The biological origin of the LDH gene introduced into the transformant of the second embodiment of the present invention is not particularly limited. Further, the number of the LDH gene introduced into the transformant of the second embodiment of the present invention may be 1 or at least 2. In the case of introducing a plurality of LDH genes into a host, a plurality of LDH genes derived from the same biological species may be introduced, or a combination of LDH genes derived from different biological species may be introduced. By appropriately adjusting the biological species and the copy number of LDH genes introduced into a *S. pombe* host, a transformant having a high lactic acid production capability can be obtained without impairing its growth ability significantly.

The transformant of the present invention is preferably a transformant containing from 3 to 5 copies of HsLDH gene (GenBank accession number: X02152.1) introduced into a *S. pombe* host, wherein a gene that is a part of a group of genes encoding pyruvate decarboxylase of the *S. pombe* host is deleted or inactivated (i.e. the above-described transformant of the first embodiment). The copy number of the HsLDH gene contained in the transformant of the present invention is more preferably from 3 to 4, most preferably 3. As shown in the following Example 1, the growth ability of a transformant, prepared by introducing 2 copies of HsLDH gene into a *S. pombe* host in which a gene that is a part of the group of genes encoding pyruvate decarboxylase is deleted or inactivated, was decreased to some extent as compared with a transformant prepared by introducing a single copy of HsLDH gene into the *S. pombe* host, while its lactic acid production capability was increased. Whereas, the growth ability of a transformant prepared by introducing 3 copies of HsLDH gene into the *S. pombe* host was almost identical to that of the transformant prepared by introducing a single copy of HsLDH gene, and its lactic acid production capability was significantly high.

[Production of Transformant]

The transformant of the present invention is prepared by using a *S. pombe* host in which a gene that is a part of the PDC gene group is deleted or inactivated, and introducing an LDH gene thereto by a genetic engineering method. Further, the transformant of the present invention can also be prepared by using a *S. pombe* host having no deletion or inactivation of PDC genes therein, and introducing an LDH gene into the *S. pombe* host by a genetic engineering method, followed by deletion or inactivation of a gene that is a part of the PDC gene group of thus obtained transformant. In the following Examples, the former method was employed to produce a desired transformant, but almost equivalent transformant can also be produced by the latter method.

In the following, the production method of a transformant will be described by referring to a method of using a *S. pombe* host in which a gene that is a part of the PDC gene group is deleted or inactivated, and introducing 3 copies of HsLDH gene thereto by a genetic engineering method.

<Host>

The *S. pombe* host may be a wild-type or a mutant-type in which a specific gene is deleted or inactivated depending on application. For deletion or inactivation of a specific gene, publicly known methods can be used. Specifically, the Latour system (Nucleic Acids Res., 2006, vol. 34, page e11, and WO2007/063919) can be used to delete the gene. Further, the gene can be inactivated by mutating the gene at a certain position by mutant screening using mutagens (Koubo Bunshi Idengaku Jikken-Hou, 1996, Japan Scientific Societies Press), random mutations using PCR (PCR Methods Appl., 1992, vol. 2, p. 28-33) and the like. As the yeast of the genus *Schizosaccharomyces* host in which a specific gene is deleted or inactivated, ones disclosed in WO2002/101038, WO2007/015470, etc. may be used.

Further, the region to be deleted or inactivated may be an ORF (open reading frame) or an expression regulatory region of a specific gene. Particularly preferred method is the PCR-mediated homologous recombination (Yeast, vol. 14, pp. 943-951, 1998) in which an ORF of a structural gene is replaced with a marker gene.

The mutant-type in which a PDC gene is deleted or inactivated is preferably used as a host for producing the transformant of the present invention. Further, a *S. pombe* host in which a specific gene other than PDC genes is deleted or inactivated, in addition to a PDC gene, may be used. Since the expression efficiency of a heterologous protein can be increased by deleting or inactivating a protease gene or the like, improvement in the lactic acid production efficiency can be expected when it is applied to the host of the present invention.

Further, the *S. pombe* to be used as a host is preferably one having a marker for selecting a transformant. For example, it is preferred to use a host which essentially requires a specific nutrient factor for growth due to deletion of a certain gene. When preparing a transformant by using a vector containing a target gene sequence, a transformant lacking the auxotrophy of the host can be obtained by using a vector carrying the deleted gene (auxotrophic complementation marker). It is possible to select the transformant by using the difference in auxotrophy between the host and the transformant.

For example, a *S. pombe* host which has been made auxotrophic for uracil by deletion or inactivation of orotidine phosphate decarboxylase (ura4 gene) is transformed with a vector containing ura4 gene (auxotrophic complementation marker), and transformants carrying the vector are obtained by selecting ones lacking uracil auxotrophy. The gene to be deleted to make an auxotrophic host is not limited to ura4 gene when it is used for selection of a transformant, and may, for example, be isopropyl malate dehydrogenase gene (leu 1 gene).

Further, a *S. pombe* strain having no deletion or inactivation of PDC genes may be used as a host for the production of a transformant. In this case, one having deletion or inactivation of the above-mentioned genes other than PDC genes (auxotrophic marker, protease gene, etc.) can be used as a host. After producing a transformant by using this host, and deleting or inactivating a gene that is a part of the PDC gene group of thus obtained transformant, the transformant of the present invention can be obtained.

<HsLDH Gene Introduction Method>

As a method for introducing HsLDH gene into a host by a genetic engineering method, publicly known methods can be used. As a method for introducing a structural gene of a heterologous protein into a *S. pombe* host, methods disclosed in JP-A-5-15380, WO95/09914, JP-A-10-234375, JP-A-2000-262284, JP-A-2005-198612, WO2011/021629, etc. may be used.

<Expression Cassette>

The expression cassette is a combination of DNA necessary for expressing a desired protein, and contains a structural gene encoding the desired gene, and a promoter and a terminator capable of functioning in a host. In the case of producing the transformant of the present invention, the expression cassette of HsLDH gene contains HsLDH gene, a promoter capable of functioning in S. pombe and a terminator capable of functioning in S. pombe. The expression cassette may contain at least one of a 5'-untranslated region and a 3'-untranslated region. Further, it may contain an auxotrophic complementation marker. The expression cassette is preferably an expression cassette containing HsLDH gene, a promoter, a terminator, a 5'-untranslated region, a 3'-untranslated region, and an auxotrophic complementation marker. Multiple copies of HsLDH gene may be present in a single expression cassette. For example, the single expression cassette may contain from 2 to 5 copies of HsLDH gene.

As the gene sequence of HsLDH gene contained in the expression cassette, a gene of the wild-type may be used as it is. However, to increase expression in a S. pombe host, it is preferred to modify the wild-type gene sequence by changing its codons to ones highly used in S. pombe.

The promoter and terminator capable of functioning in S. pombe may be ones which can maintain expression of LDH by functioning in the transformant even if it becomes acidic (even when it becomes pH 6 or lower) due to the accumulation of lactic acid by the transformant of the present invention. As the promoter capable of functioning in S. pombe, a promoter endogenous to S. pombe (preferably one having a high transcriptional activity), or a promoter exogenous to S. pombe (such as a promoter derived from a virus) may be used. Further, two or more types of promoters may be contained in the vector.

As the promoter endogenous to S. pombe, an alcohol dehydrogenase gene promoter, a nmt1 gene promoter involved in thiamine metabolism, a fructose 1,6-bisphosphatase gene promoter involved in glucose metabolism, an invertase gene promoter involved in catabolite repression (WO99/23223) or a heat shock protein gene promoter (WO2007/26617) may, for example, be mentioned.

As the promoter exogenous to S. pombe, promoters derived from an animal cell virus disclosed in JP-A-5-15380, JP-A-7-163373 and JP-A-10-234375 may, for example, be mentioned. Among these promoters, a hCMV promoter and a SV40 promoter are preferred.

As the terminator capable of functioning in S. pombe, a terminator endogenous to S. pombe or a terminator exogenous to S. pombe may be used. Further, two or more types of terminators may be contained in the vector.

As the terminator, terminators derived from human disclosed in JP-A-5-15380, JP-A-7-163373 and JP-A-10-234375 may, for example, be mentioned, and human lipocortin-I terminator is preferred.

<Vector>

The transformant of the present invention has an expression cassette containing HsLDH gene in its chromosome or as an extrachromosomal gene. Here, having the expression cassette in its chromosome means that the expression cassette is integrated into at least one position of the chromosome of a host cell, and having as an extrachromosomal gene means that a plasmid containing the expression cassette is contained in the cell. The transformant which has an expression cassette containing HsLDH gene can be obtained by transforming a S. pombe host with a vector containing the expression cassette of HsLDH gene.

The vector can be produced by integrating the expression cassette into a vector having a circular DNA structure or a linear DNA structure. In the case of preparing a transformant in which the expression cassette is maintained in the host cell as an extrachromosomal gene, the vector is preferably a plasmid which contains a sequence required for replication in the host cell, i.e. Autonomously Replicating Sequence (ARS). On the other hand, in the case of preparing a transformant in which the expression cassette is integrated into the chromosome of a host cell, the vector is preferably introduced into the host cell as one having a linear DNA structure and containing no ARS. For example, the vector may be a vector consists of linear DNA, or a vector having a circular DNA structure and containing a restriction enzyme recognition site for cutting it open to linear DNA at the time of its introduction into the host cell. When the vector is a plasmid containing ARS, it can be introduced into a host after eliminating the ARS portion to form a linear DNA structure, or after the ARS portion is cut open to a linear DNA structure in which the function of ARS is inactivated.

The expression vector preferably has a marker for selecting a transformant. As the marker, ura4 gene (auxotrophic complementation marker) and isopropyl malate dehydrogenase gene (leu1 gene) may, for example, be mentioned.

It is preferred to introduce HsLDH gene into the chromosome of S. pombe. By introducing HsLDH gene into a chromosome, a transformant having a high passage stability can be obtained. Further, the transformant of the present invention containing from 3 to 5 copies of HsLDH gene may be one containing from 3 to 5 copies of HsLDH gene introduced into one position of the chromosome, or one containing single copy introduction of HsLDH gene at from 3 to 5 positions of the chromosome.

As a method for introducing HsLDH gene into a chromosome, publicly known methods can be used. For example, by the method disclosed in JP-A-2000-262284, multiple copies of HsLDH gene can be introduced into a chromosome. Further, single copy of HsLDH gene can be introduced into a chromosome. Further, as described below, single or multiple copies of LDH gene can be introduced into multiple positions on a chromosome.

The method for introducing HsLDH gene into the chromosome of S. pombe is preferably a homologous recombination method using a vector containing an expression cassette containing HsLDH gene and a recombination region.

The recombination region of the vector is a region having a nucleotide sequence which can induce homologous recombination with a target site in the chromosome of S. pombe at which homologous recombination is to be achieved. Further, the target site is a site to become a target for integration of an expression cassette in the chromosome of S. pombe. The target site can be designed freely by letting the recombination region of the vector have a nucleotide sequence which induces homologous recombination with the target site.

The recombination region is required to have a nucleotide sequence homology of at least 70% with the nucleotide sequence of the target site. Further, the nucleotide sequence homology between the recombination region and the target site is preferably at least 90%, more preferably at least 95%, in view of increasing the efficiency of homologous recombination. By using a vector having such a recombination region, the expression cassette is integrated into the target site by homologous recombination.

The length (number of base pairs) of the recombination region is preferably from 20 to 2,000 bp. When the length of the recombination region is at least 20 bp, homologous recombination is likely to be induced. Further, when the length of the recombination region is at most 2,000 bp, reduction in the homologous recombination efficiency due to too large vector size is likely to be prevented. The length of the recombination region is preferably at least 100 bp, more preferably at least 200 bp. Further, the length of the recombination region is preferably at most 800 bp, more preferably at most 400 bp.

The vector may contain another DNA region in addition to the above-described expression cassette and recombination region. For example, a replication origin region called "ori" which is necessary for replication in *E. coli*, an antibiotic resistance gene (neomycin resistance gene or the like), etc. may be mentioned. These are genes generally required for the construction of a vector using *E. coli*. The replication origin region is preferably removed when integrating the vector into the chromosome of the host, as described below.

In a case where LDH gene is integrated into a chromosome, the vector is preferably introduced into a *S. pombe* cell in the form of a linear DNA structure. That is, in the case of using a vector having a circular DNA structure like a usual plasmid DNA, the vector is preferably cut open to a linear form by a restriction enzyme before its introduction into the *S. pombe* cell.

In this case, the vector having a circular DNA structure is cut open at a position within the recombination region. The resulting vector has parts of the recombination regions exist at both ends and is integrated entirely into the target site of a chromosome by homologous recombination.

The vector may be constructed by other methods without cutting a vector having a circular DNA structure so long as a linear DNA structure having parts of the recombination region at both ends can be obtained.

As the vector, a plasmid derived from *E. coli* such as pBR322, pBR325, pUC118, pUC119, pUC18, pUC19 or the like may suitably be used.

In this case, it is preferred that the replication origin region called "ori" required for replication in *E. coli* is removed from the plasmid vector to be used for homologous recombination. Thus, the integration efficiency at the time of integrating the above-described vector into a chromosome can be increased.

The method for constructing the vector in which the replication origin region is removed is not particularly limited, but is preferably the method disclosed in JP-A-2000-262284. That is, it is preferable to preliminarily construct a precursor vector carrying the replication origin region at a position to be cut within the recombination region so that the replication origin region will be cut-off from the vector at the time of preparing a linear DNA structure. Thus, a vector in which the replication origin region is removed can be obtained easily.

Further, it may be a method wherein a precursor vector containing an expression cassette and a recombination region is constructed by using the expression vectors and their construction methods disclosed in JP-A-5-15380, JP-A-7-163373, WO96/23890, JP-A-10-234375, and then the replication origin region is removed from the precursor vector by using a usual genetic engineering method to obtain a vector to be used for homologous recombination.

<Target Site>

The target site for integration of the vector may be present in only one position of the chromosome of *S. pombe*, or may be present in two or more positions thereof. When the target site is present in two or more positions, the vector can be integrated into two or more positions of the chromosome of *S. pombe*. Further, when multiple copies of HsLDH gene are contained in a single vector, the multiple copies of HsLDH gene can be integrated into one position of the target site. Further, the expression cassette may be integrated into two or more types of target sites by using two or more types of vectors having recombination regions corresponding to the respective target sites. According to this method, multiple copies of LDH gene can be integrated into the chromosome of *S. pombe*, thereby to increase the expression amount of LDH and improve the productivity of lactic acid.

When the expression cassette is integrated into one target site, the target site disclosed in JP-A-2000-262284 may, for example, be used. By using two or more types of vectors having different recombination regions, each of the vectors can be integrated into different target sites. However, this method becomes complicated in the case of integrating vectors into two or more positions of the chromosome.

Assuming that nucleotide sequences which are substantially identical to one another and present in plural positions of a chromosome can be used as target sites and vectors can be integrated into the respective plural positions of target sites, vectors can be integrated into two or more positions of the chromosome by using a single type of vector. The nucleotide sequences which are substantially identical to one another means that the homology between the nucleotide sequences is at least 90%. The homology among the target sites is preferably at least 95%. Further, the length of the nucleotide sequences which are substantially identical to one another is a length encompassing the recombination region of a vector, and is preferably at least 1,000 bp. As compared with a case wherein multiple copies of HsLDH gene are integrated into one target site, even if the integration numbers of HsLDH gene are the same, when HsLDH gene is integrated into plural target sites in a dispersed manner, drop-out of every HsLDH gene from the chromosome is less likely to occur during cultivation, whereby the maintenance stability during cultivation of the transformant increases.

When integrating an expression cassette containing a single copy of LDH gene into each of the target sites present in three positions of the chromosome, as the target site to be integrated with the expression cassette, three positions selected from a region near the ura4 gene locus, a region near the leu1 gene locus, a region near the adh1 gene locus, a region near the gpd1 gene locus, a region near the eno101 gene locus, a region near the leu1 gene locus, and a region near the gpm1 gene locus may, for example, be mentioned.

Here, "a region near the X gene locus" means that a region ranging from 10 kbp (10,000 bp) upstream of the upstream end of an ORF of X gene to 10 kbp (10,000 bp) downstream of the downstream end of the ORF, and having no ORF of other gene.

The transformant of the present invention is preferably one in which HsLDH gene is introduced into a target site selected from a region near the eno101 gene locus, a region near the leu1 gene locus, and a region near the gpm1 gene locus. The transformant of the present invention is preferably one in which HsLDH gene is introduced into a region selected from a region that comprises from 10,000 bp upstream to 10,000 bp downstream of the eno101 gene locus, a region that comprises from 10,000 bp upstream to 10,000 bp downstream of the leu1 gene locus, and a region that comprises from 10,000 bp upstream to 10,000 bp downstream of the gpm1 gene locus of *S. pombe* chromosome, and is more preferably one in which the gene is introduced into a region selected from a region that comprises from 5,000 bp upstream to 5,000 bp downstream of the eno101 gene locus, a region that comprises from 5,000 bp upstream to 5,000 bp downstream of the leu1 gene locus, and a region that comprises from 5,000 bp upstream to 5,000 bp downstream of the gpm1 gene locus of *S. pombe* chromosome.

The target site present in plural positions of the chromosome is preferably transposon gene Tf2. Tf2 is a transposon gene which exists in every three chromosomes (monoploid) of *S. pombe* at 13 positions in total and has a length (number of base pairs) of about 4,900 bp, with a nucleotide sequence homology of 99.7% (refer to the below-identified reference).

Nathan J. Bowen et al., "Retrotransposons and Their Recognition of pol II Promoters: A Comprehensive Survey of the Transposable Elements From the Complete Genome Sequence of *Schizosaccharomyces pombe*", Genome Res., 2003 13: 1984-1997.

It is possible to integrate a vector into only one position of Tf2 which exists in 13 positions of the chromosome. In such a case, by integrating a vector containing two or more copies of LDH gene, a transformant having two or more copies of LDH gene can be obtained. Further, by integrating a vector into two or more positions of Tf2, a transformant having two or more copies of LDH gene can be obtained. In this case, by integrating a vector containing two or more copies of LDH gene, a transformant having even more copies of LDH gene can be obtained.

<Transformation Method>

As the transformation method, any publicly known transformation method may be used. Such a transformation method may, for example, be a conventional method like a lithium acetate method, electroporation method, spheroplast method, glass-beads method, or the like., and a method disclosed in JP-A-2005-198612. Further, a commercially available yeast transformation kit may be used.

As the method for transforming a *S. pombe* host by a homologous recombination method, a publicly known homologous recombination method can be used. The transformation method for producing the transformant of the present invention is preferably a method of using a *S. pombe* host in which a gene that is a part of the above-mentioned PDC gene group is deleted or inactivated, and integrating an expression cassette into the chromosome by using the above-described vector. According to this method, the transformant of the present invention can be produced conveniently.

For the production of a transformant, usually, after carrying out homologous recombination, the obtained transformants are subjected to selection. The selection may, for example, be carried out as follows. Screening is carried out by a culture broth which can select transformants by the above-mentioned auxotrophic marker, and two or more colonies are selected among the obtained colonies. Then, after cultivating them separately in a liquid broth, the expression amount of a heterologous protein (in the present invention, HsLDH) in each liquid broth is measured so as to select a transformant showing higher expression amount of the heterologous protein. The number of a vector and the number of an expression cassette integrated into the chromosomes can be identified by subjecting the selected transformants to a genomic analysis using pulse-field gel electrophoresis.

The number of a vector integrated into the chromosomes can be adjusted to some extent by adjusting integration conditions, etc., but the integration efficiency and integration number also change due to the size (number of base pairs) and structure of the vector.

In general, as the number of expression cassette becomes large, the expression efficiency of LDH is expected to increase, and further, the production efficiency of lactic acid is also expected to increase. Therefore, it is considered that the expression amount of LDH can be increased and the productivity of lactic acid can be improved by integrating multiple copies of LDH gene into *S. pombe* chromosome. However, it is also considered that when the number of expression cassettes is too large, the load on the survival and growth of cells becomes large and the production efficiency of lactic acid may thereby be lowered. On the other hand, by using a single expression vector which contains multiple copies of genes, multiple copies of LDH gene can be integrated into the chromosome, while reducing the number of the expression cassette integrated into the chromosome. However, it is considered that the chromosomal integration efficiency decreases as the size of a vector becomes large, whereby it becomes difficult to increase the integration number of a vector, and as a result, production of a transformant itself becomes difficult.

The present inventors had considered that it is necessary to select a foreign LDH gene which has a high expression efficiency in *S. pombe* and expresses an LDH of high activity, for obtaining a *S. pombe* transformant having a higher lactic acid production efficiency even in the case of integrating a relatively small number of an expression cassette having an appropriate size into a chromosome. Then, they have found that a transformant which has a significantly higher lactic acid production efficiency, as compared with a transformant integrated with a single copy or 2 copies of HsLDH gene, can be obtained without impairing its growth ability, when from 3 to 5 copies of HsLDH gene are introduced into a *S. pombe* transformant having deletion or inactivation of a gene that is a part of the PDC gene group.

[Method for Producing Lactic Acid]

The method for producing lactic acid of the present invention is a method of cultivating the transformant of the present invention in a culture broth, and then recovering lactic acid from the culture broth.

By cultivating the transformant of the present invention in a culture broth containing a saccharide, pyruvic acid obtained from the saccharide by the glycolytic pathway is reduced by LDH to generate lactic acid, and the lactic acid generated into the culture broth is recovered from the culture broth to produce lactic acid.

As the culture broth for producing lactic acid, a conventional yeast culture medium containing a saccharide can be used, and it may further contain nitrogen sources, inorganic salts and the like which can be utilized by *S. pombe* and can carry out the cultivation of *S. pombe* efficiently. As the culture broth, a natural medium or a synthetic medium may be used.

As the carbon sources, saccharides such as glucose, fructose and sucrose may, for example, be mentioned. As the nitrogen sources, inorganic acids or inorganic ammonium salts such as ammonia, ammonium chloride, and ammonium acetate, peptone casamino acid, and yeast extract may, for example, be mentioned. As inorganic salts, magnesium phosphate, magnesium sulfate and sodium chloride may, for example, be mentioned. In addition, a fermentation accelerator such as proteolipid or the like may be contained.

According to the lactic acid production method of the present invention, it is preferred to use a culture broth which contains especially glucose as the saccharide. Glucose concentration of the culture broth (100 mass %) in the initial stage of cultivation is preferably at least 1 mass %, more preferably from 1 to 50 mass %, further preferably from 2 to 16 mass %. Since the glucose concentration decreases as the cultivation proceeds, it is preferred to continue the cultivation by adding glucose as the case requires. Glucose concentration at the final stage of cultivation may be at most 1 mass %. Further, in a case where the cultivation is carried out continuously by circulating the culture broth while separating lactic acid, it is preferred to maintain the above-mentioned glucose concentration. When the glucose concentration is made to be at least 2 mass %, the productivity of lactic acid increases further. Further, when the glucose in the culture broth is made to be at most 16 mass %, the production efficiency of lactic acid increases further.

Further, in order to increase the lactic acid productivity, it is preferred to carry out high density cultivation. In the high density cultivation, the initial cell concentration of the transformant in the culture broth is made to be preferably from 0.1 to 5 g/L, on a dry cell weight basis. The initial cell concentration of the transformant in the culture broth is made to be more preferably from 0.2 to 2 g/L, on a dry cell weight basis. By increasing the initial cell concentration, high productivity can be accomplished in a short period of time. Further, if the initial cell concentration is too high, a problem such as agglomeration of cells or a decrease in the purification efficiency is likely to occur.

Further, the cell concentration shown in Examples given hereinafter, is a value calculated from the absorbance of light at a wavelength of 660 nm (OD660) measured by a visible-ultraviolet spectrometer V550 manufactured by JASCO corporation. OD660=1 corresponds to 0.2 g/L of the dry weight of yeast and 0.8 g/L of the wet weight.

For the cultivation, a conventional yeast cultivation method may be used, and for example, the cultivation may be carried out with shaking or stirring.

The cultivation temperature is preferably from 23 to 37° C. The cultivation time may suitably be determined.

The cultivation may be carried out by batch culture or continuous culture. For example, after carrying out cultivation by batch culture, the cells may be separated from the culture broth to obtain a culture broth containing lactic acid. Whereas, in the continuous cultivation method, for example, a part of the culture broth is withdrawn from the culture tank during cultivation; a culture supernatant is collected while separating lactic acid from the withdrawn culture broth; glucose or a fresh culture broth is added to the culture supernatant and then returned to the culture tank. This operation is repeated to continuously carry out cultivation. By carrying out continuous culture, the lactic acid productivity increases further.

Since a S. pombe particularly excellent in acid resistance is used in the method for producing lactic acid using the transformant of the present invention, even in a case where pH becomes low (approximately a pH of 2 to 4) due to the accumulation of lactic acid, lactic acid can be produced without carrying out neutralization. Thus, even after the pH of the culture broth becomes 3.5 or lower, lactic acid can be produced by continuous culture which further continues the cultivation. The pH at the final stage of cultivation or the pH during continuous culture is preferably at most 3.5, particularly preferably from 2.3 to 3.5. In order to increase the productivity of lactic acid, it is preferred to continue the cultivation even after the pH of the culture broth becomes to be 3.5 or lower. Since the transformant of the present invention is excellent in acid resistance, its cultivation can be continued without neutralizing the lactic acid produced by the transformant in the culture broth.

The recovery of lactic acid from a culture broth can be carried out by a conventional method. Particularly, it is preferred to recover lactic acid, without carrying out neutralization of the lactic acid in the culture broth, by separating lactic acid from the culture broth. For example, a method in which cells are separated from a culture broth after completion of the cultivation by centrifugation and then extraction is carried out with diethyl ether, ethyl acetate and the like after adjusting the pH to 1 or lower, a method in which, after adsorption to an ion exchange and subsequent washing, elution is carried out, a method in which impurities are removed by using activated carbon, a method in which distillation is carried out after allowing to react with an alcohol in the presence of an acid catalyst, and a method in which separation is carried out by using a separation membrane may be mentioned. Further, in some cases, the recovery of lactic acid may be carried out by neutralizing the lactic acid in a culture broth and separating the culture broth and the lactic acid salt. For example, the recovery of lactic acid can be carried out by a method in which the lactic acid in a culture broth is converted into a calcium salt or a lithium salt and then the neutralized salt is crystallized.

Since a S. pombe particularly excellent in acid resistance is used in the method for producing lactic acid of the present invention, the production of lactic acid can be carried out conveniently with a high productivity without carrying out neutralization with an alkali. Further, since the efficiency of ethanol fermentation is lowered due to the deletion or inactivation of a gene that is a part of the PDC gene group, the saccharide-based lactic acid yield (ratio of the amount of lactic acid produced to the amount of saccharide consumed) increases. In the present invention, the saccharide-based lactic acid yield can be easily increased to 50% or higher. In some cases, the saccharide-based lactic acid yield reaches 70% or higher. Further, the method for producing lactic acid of the present invention is also suitable for a high density cultivation in which the cultivation is carried out under a high concentration of glucose and by a high concentration of transformant.

EXAMPLES

Now, the present invention will be described in further detail with reference to Examples and Comparative Examples. However, it should be understood that the present invention is by no means thereby restricted. Further, In the following Examples, the term "%" means "mass %" unless otherwise noted.

Example 1

By using a S. pombe host, a transformant in which PDC2 gene is deleted and 3 copies of HsLDH gene is introduced was prepared.

<Preparation of S. pombe PDC2 Gene Deletion Strain>

A uracil-auxotrophic strain ARC010 of S. pombe (genotype: h-, leu1-32 ura4-D18) (refer to WO 2007/015470) was transformed with a pdc2 deletion fragment in accordance with Tohoda's method (refer to U.S. Pat. No. 6,235,499), thereby to obtain a transformant in which the fragment is introduced into a region near the pdc2 gene locus of the S. pombe genome. The transformant was subjected to FOA treatment in accordance with the Latour system (Nucleic Acids Res., 2006, vol. 34, page e11, and WO2007/063919) to prepare a deletion strain (IGF 543 strain) in which PDC2 gene (systematic ID: SPAC1F8.07c) was deleted.

For the preparation of the pdc2 deletion fragment (2,811 bp, SEQ ID NO: 11), the whole genomic DNA prepared from ARC032 strain (genotype: h-) of S. pombe (refer to WO 2007/015470) by using DNeasy (manufactured by QIA- GEN) was used as the template, and the 8 types of synthetic oligo-DNA (manufactured by Operon) having the nucleotide sequences shown in Table 1 were used.

[Table 1]

Specifically, each of UP region, OL region, and DN region was prepared by a PCR amplification of using KOD-Dash (manufactured by Toyobo Co. Ltd.) with UF and UR, OF and OR, and DF and DR, respectively. Then, using these regions as respective templates, full-length deletion fragments were prepared by a similar PCR amplification of using FF and FR. At the time of preparing the full-length deletion fragments, the two types of synthetic oligo-DNA (manufactured by Operon) shown in Table 2 were used, the whole genomic DNA similarly prepared from ARC032 strain was used as a template, and a ura4 region fragment prepared by a similar PCR amplification was also used as a template.

[Table 2]

The growth rate of thus obtained S. pombe PDC2 gene deletion strain (IGF543 strain, h-, leu1-32 ura4-D18 pdc2-D23) was found to be slow. Therefore, in order to restore its growth rate, IGF543 strain was streaked on YES plate (yeast extract 0.5%/glucose 3%/SP supplement) and cultured at 25° C., and then thus obtained colonies were sub-cultured in YPD medium (yeast extract 1%/peptone 2%/glucose 2%), and cultured at 25° C. Then, by using a culture broth having sufficiently grown cells, a glycerol stock was prepared and preserved at −80° C. The above-mentioned procedure was repeated until an appropriate growth rate was obtained, and a strain restored its growth rate was selected (the name IGF543 was succeeded).

<Preparation of S. pombe HsLDH Gene Single Copy Introduction Strain>

At first, single-locus integration type recombinant vector pSM-HsLDH vector (4,562 bp, FIG. 1) containing a HsLDH expression cassette was prepared. The pSM-HsLDH vector was prepared by DNA synthesis as a DNA fragment having a nucleotide sequence represented by SEQ ID NO: 12.

Then, IGF543 strain was transformed by pSM-HsLDH vector. By this operation, the HsLDH expression cassette was introduced into a region near the gpm1 gene locus of the genome. Thus obtained transformant strain (HsLDH gene single copy introduction strain) was named as ASP3494 strain.

<Preparation of S. pombe HsLDH Gene 2 Copies Introduction Strain>

ASP3494 strain was transformed in accordance with the method of Bahler et al. (Yeast, 1998, vol. 14, pp. 943-951) with a restriction enzyme BsiWI digest of single-locus integration type recombinant vector pSL17-HsLDH containing ihc1 promoter (refer to Patent Document 3). By this operation, the expression cassette was introduced into a region near the leu1 gene locus of the genome, thereby to prepare a transformant strain in which a single copy of HsLDH gene regulated by hCMV promoter is introduced at the region near the gpm1 gene locus and another single copy of HsLDH gene regulated by ihc promoter is introduced at the region near the leu1 gene locus (2 copies of HsLDH gene in total). Thus obtained transformant strain (HsLDH gene 2 copies introduction strain) was named as ASP4121 strain.

<Restoration of Uracil Auxotrophy>

The ura4 gene introduced into the S. pombe genome by pSM-HsLDH vector is likely to drop-out from the genome by homologous recombination, since it is put between two hCMV promoter sequences.

Therefore, ASP4121 strain was subjected to FOA treatment to restore its uracil auxotrophy.

<Preparation of S. pombe HsLDH Gene 3 Copies Introduction Strain>

Figure 2:
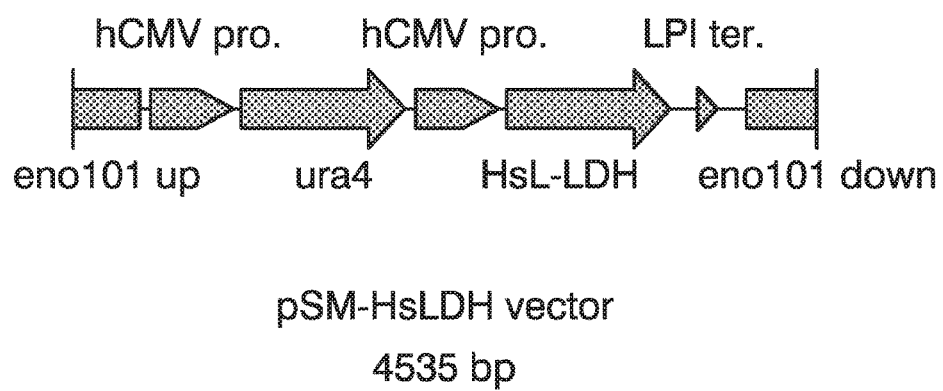
FIG. 2 is a schematic figure illustrating the structure of recombinant vector pSN-HsLDH vector.

At first, single-locus integration type recombinant vector pSN-HsLDH vector (4,535 bp, FIG. 2) containing a HsLDH expression cassette was prepared. The pSN-HsLDH vector was prepared by DNA synthesis as a DNA fragment having a nucleotide sequence represented by SEQ ID NO: 13.

Then, ASP4121 strain was subjected to FOA treatment to restore its uracil auxotrophy, and thus obtained transformant strain was transformed by pSN-HsLDH vector. By this operation, the HsLDH expression cassette was introduced into a region near the eno101 gene locus of the genome, thereby to prepare a transformant strain in which a single copy of HsLDH gene regulated by hCMV promoter is introduced at the region near the gpm1 gene locus, a single copy of HsLDH gene regulated by ihc promoter is introduced at the region near the leu1 gene locus, and a single copy of HsLDH gene regulated by hCMV promoter is introduced at the region near the eno101 gene locus (3 copies of HsLDH gene in total). The obtained transformant strain (HsLDH gene 3 copies introduction strain) was named as ASP4956 strain.

<Restoration of Uracil Auxotrophy>

In the same manner as for the case of using pSM-HsLDH vector, the ura4 gene introduced into the S. pombe genome by pSN-HsLDH vector is likely to drop-out from the genome by homologous recombination, since it is sandwiched by two hCMV promoter sequences.

Therefore, ASP4956 strain was subjected to FOA treatment to restore its uracil auxotrophy.

<Complementation of Uracil Auxotrophy>

ASP4956 strain was subjected to FOA treatment to restore its uracil auxotrophy, and thus obtained transformant strain was transformed with a DNA fragment containing ura4 gene (3,277 bp, SEQ ID NO: 14), thereby to prepare a transformant strain lacking uracil auxotrophy. The obtained transformant strain (HsLDH gene 3 copies introduction and auxotrophy-lacking strain) was named as ASP5019 strain.

<Cultivation Test>

In terms of the growth ability and the lactic acid production capability, ASP5019 strain was compared with ASP3509 strain, ASP2914 strain, ASP3619 strain, ASP3621 strain, ASP3631 strain, ASP3622 strain and ASP3623 strain disclosed in Patent Document 3. ASP3509 strain was a strain prepared by introducing a single copy of HsLDH gene into IGF543 strain, ASP2914 strain was a strain prepared by introducing 2 copies of HsLDH gene into IGF543 strain, ASP3619 strain was a strain prepared by introducing a single copy of HsLDH gene and a single copy of LbLDH gene (LDH gene of *Lactobacillus bulgaricus*) into IGF543 strain, ASP3621 strain was a strain prepared by introducing a single copy of HsLDH gene and a single copy of SaLDH gene (LDH gene of *Staphylococcus aureus*) into IGF543 strain, ASP3631 strain was a strain prepared by introducing a single copy of HsLDH gene and a single copy of LpLDH gene into IGF543 strain, ASP3622 strain was a strain prepared by introducing a single copy of HsLDH gene and a single copy of LplLDH gene (LDH gene of *Lactobacillus plantarum*) into IGF543 strain, and ASP3623 strain was a strain prepared by introducing a single copy of HsLDH gene and a single copy of PaLDH gene (LDH gene of *Pediococcus acidilactici*) into IGF543 strain.

Each transformant strain was inoculated into 100 ml of YPD6 liquid medium (yeast extract 1%, peptone 2% and glucose 6%) contained in a 500 mL Sakaguchi flask (manufactured by AGC Techno Glass, Co. Ltd.) at an initial cell concentration of 0.04 g (on a dry cell weight basis)/L, and cultivated for 20 hours at a temperature of 32° C. under shaking conditions of 110 rpm shaking speed and 7 cm shaking stroke. The cultivation was terminated after measuring OD660 of the culture broth, and then cells were collected. Thus obtained cells were inoculated into 4.5 mL of a 11.1% glucose aqueous solution contained in a test tube having a diameter of 18 mm and a length of 150 mm at an initial cell concentration of 36 g (on a dry cell weight basis)/L, and cultivated for 3 hours at a temperature of 32° C. under shaking conditions of 43.5° shaking angle, 110 rpm and 7 cm stroke. At the end of the cultivation, the lactic acid concentration (g/L) of the fermentation liquor was measured. The cell concentration (g (on a dry cell weight basis (dcw))/L) of the culture broth after cultivating 20 hours and the lactic acid concentration (g/L) after fermenting 3 hours of each transformant are shown in Table 3.

[Table 3]

Figure 3:
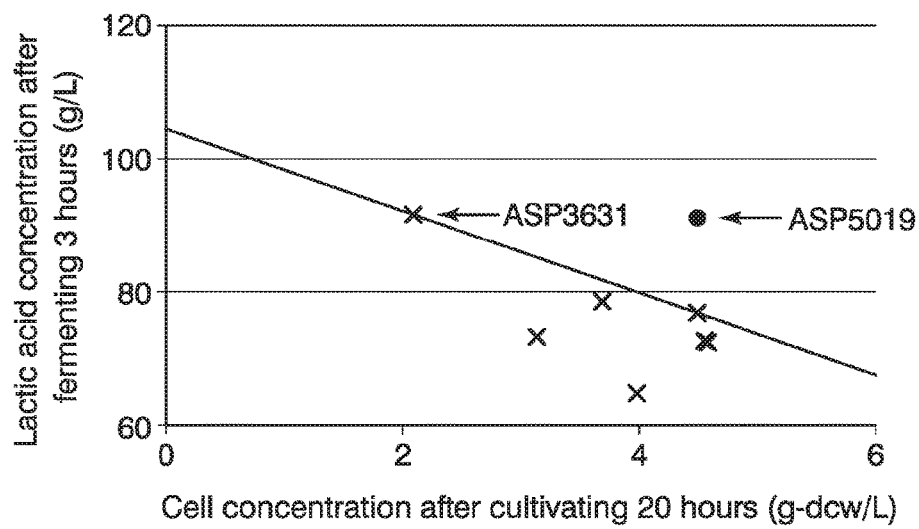
FIG. 3 is a dispersion diagram showing a lactic acid concentration (g/L) after fermenting 3 hours (vertical axis) and a cell concentration (g (on a dry cell weight basis (dcw))/L) of a culture broth after cultivating 20 hours (horizontal axis), of each transformant in Example 1.

When ASP3509 strain prepared by introducing a single copy of HsLDH gene was compared with ASP2914 strain prepared by introducing 2 copies of HsLDH gene, ASP2914 strain was found to have higher lactic acid concentration after fermenting 3 hours, and ASP3509 was found to have higher OD660 value after cultivating 20 hours. Further, the cell concentration after cultivating 20 hours of ASP3631 strain, which showed a significantly high lactic acid concentration after fermenting 3 hours, was found to be very low. The results of Table 3 are represented as a dispersion diagram (FIG. 3) showing a lactic acid concentration (g/L) after fermenting 3 hours (vertical axis) and a cell concentration (g (on a dry cell weight basis (dcw))/L) of a culture broth after cultivating 20 hours (horizontal axis). As illustrated in FIG. 3, there is a tendency that as the lactic acid production capability of a transformant increases, the growth ability decreases. The straight line found in FIG. 3 is a straight line connecting the plots of ASP3509 strain and ASP3631 strain. From the tendency, it can be expected that a transformant strain prepared by introducing 3 copies of HsLDH gene shows higher lactic acid production capability and lower growth ability as compared with a transformant strain prepared by introducing 2 copies of HsLDH gene (ASP2914 strain), and that if the lactic acid production capability of a transformant strain prepared by introducing 3 copies of HsLDH gene is higher than that of ASP3631 strain, the growth ability of the strain is lower than that of ASP3631 strain. However, in spite of this expectation, ASP5019 strain prepared by introducing 3 copies of HsLDH gene was found to have a high lactic acid production capability at the almost same level as ASP3631 strain and have a sufficient growth ability at the almost same level as ASP3509 strain.

Example 2

Each of ASP5019 strain and ASP3631 strain used in Example 1 was cultivated in a flask to compare the growth ability and the lactic acid production capability of respective strains.

Specifically, each transformant strain was inoculated into YES liquid culture medium (yeast extract 5 g/L, glucose 30 g/L, adenine 1 g/L, histidine 1 g/L, leucine 1 g/L, uracil 1 g/L, and ricin 1 g/L), and cultivated for 30 hours at a temperature of 32° C. under a shaking condition of 110 rpm. At the end of the cultivation, cells were collected. Thus collected cells were inoculated into a 3 L jar fermenter filled with a culture medium having the composition shown in Table 4 and appropriate amounts of trace elements and vitamins added thereto, and then cultivated by fed-batch culture for 60 hours at a temperature of 32° C. under a OD cascade control. At the end of the cultivation, OD660 of the culture broth was measured.

Then, from the culture broth obtained at the end of the cultivation, cells were separated by centrifugation and then inoculated into a 11.1% glucose aqueous solution at an initial cell concentration of 36 g (on a dry cell weight basis)/L (OD660=180) to prepare a fermentation liquor. Thereafter, fermentation was carried out for 7 hours in a test tube. At the end of the fermentation, the lactic acid concentration (g/L) of the fermentation liquor was measured.

[Table 4]

Figure 4:
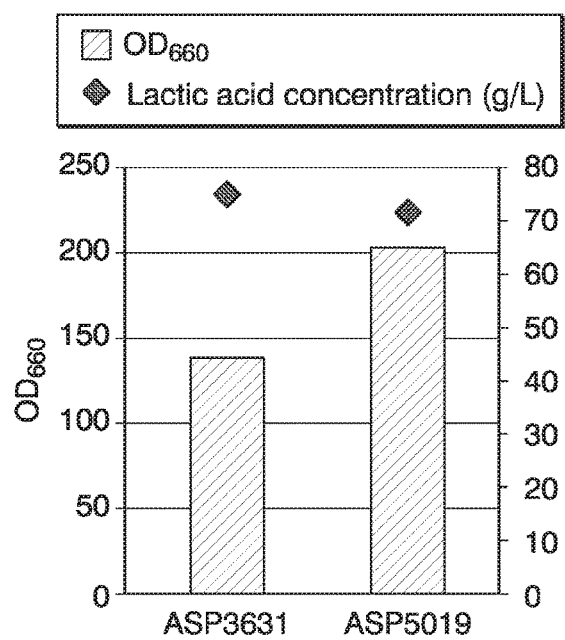
FIG. 4 is a graph showing the measurement results of OD660 of a culture broth after cultivating 60 hours and a lactic acid concentration (g/L) of a fermentation liquor after fermenting 3 hours, of each transformant in Example 2.

With respect to the each transformant, the OD660 of the culture broth after cultivating 60 hours and the lactic acid concentration (g/L) of the fermentation liquor after fermenting 7 hours were measured, and the results are shown in FIG. 4. ASP5019 strain was found to have a high lactic acid production capability like ASP3631 strain, and its growth ability was confirmed to be significantly higher than that of ASP3631 strain.

Example 3

ASP5019 strain and ASP3631 strain used in Example 1 were cultivated by continuous culture to compare their lactic acid production capabilities.

Specifically, cells obtained by 60-hour fed-batch culture in the same manner as in Example 2 were collected, and thus collected cells were inoculated into a fermentation medium having the composition of Table 5 and appropriate amounts of trace elements and vitamins added thereto, at an initial cell concentration of 36 g (on a dry cell weight basis)/L (OD660=180), to prepare a fermentation liquor. 0.5 L of the fermentation liquor was transferred to a 1 L jar fermenter, and circulated through a crossflow microfiltration membrane. Then, a continuous fermentation was carried out for 200 hours or longer at 28° C. by supplying a fermentation medium at a constant flow rate and withdrawing a membrane filtrate. At that time, a dilution rate of 0.066 (1/h) was employed. In the continuous fermentation, a microfiltration membrane having a pore size smaller than the size of each cell was used, whereby the cells were returned to the tank and recycled during the continuous fermentation for 200 hours or longer. The neutralization of pH using an alkali was not carried out.

[Table 5]

Figure 5:
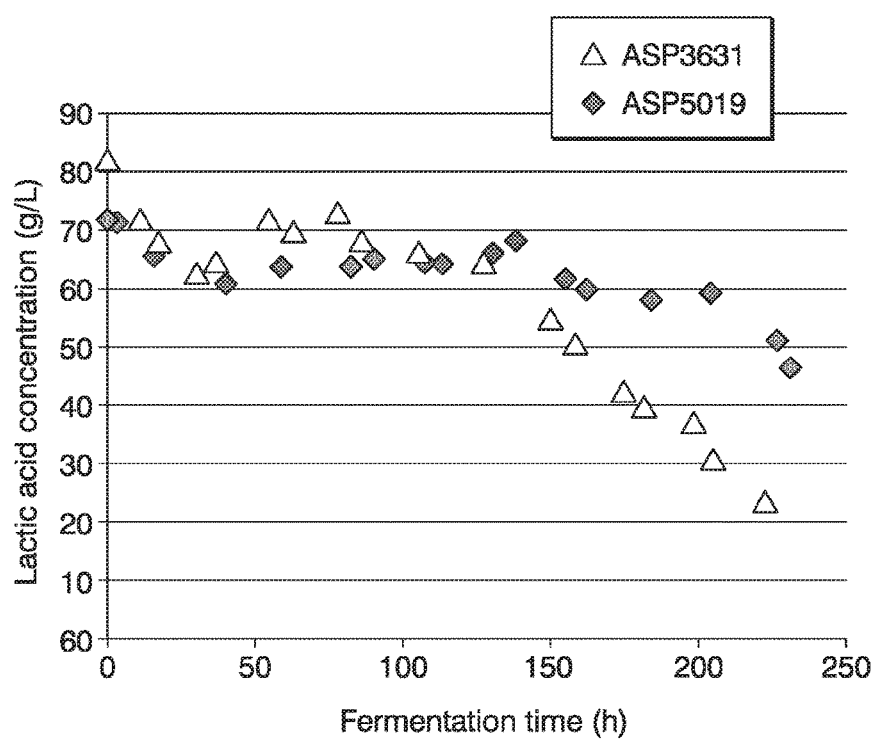
FIG. 5 is a graph showing time-course changes in a lactic acid concentration (g/L) of a fermentation liquor in the continuous fermentation of each transformant in Example 3.

The time course-changes in the lactic acid concentration (g/L) of the fermentation liquor in the continuous fermentation are shown in FIG. 5. As a result of the continuous fermentation for 200 hours or longer, from the start of fermentation to the point of 120 hours after fermentation, ASP5019 strain and ASP3631 strain were almost identical in terms of their lactic acid concentrations, and showed constant values. After the point of 150 hours after fermentation, a decrease trend was observed. However, the decrease trend of ASP5019 strain was milder than that of ASP3631 strain. These results indicate that ASP5019 strain has a significantly high lactic acid production capability under conditions of long-term operation and high oxygen.

INDUSTRIAL APPLICABILITY

Since the transformant of the present invention and the lactic acid production method using the transformant can produce lactic acid with a high productivity even at a low pH without carrying out neutralization with an alkali, they can suitably be used for an industrial production method of lactic acid.

What is claimed is:

1. A transformant comprising:
   3 copies of a human lactate dehydrogenase gene that are introduced into a *Schizosaccharomyces pombe* host, wherein a gene encoding pyruvate decarboxylase 2 of the *Schizosaccharomyces pombe* host is deleted or inactivated.

2. The transformant according to claim 1, wherein the 3 copies of the human lactate dehydrogenase gene are integrated into *Schizosaccharomyces pombe* chromosome.

3. The transformant according to claim 2, wherein each of the 3 copies of the human lactate dehydrogenase gene is introduced into a region that comprises from 10,000 bp upstream to 10,000 bp downstream of an eno101 gene locus, a region that comprises from 10,000 bp upstream to 10,000 bp downstream of a leu1 gene locus, and a region that comprises from 10,000 bp upstream to 10,000 bp downstream of a gpm1 gene locus.

4. A process for producing the transformant according to claim 1, the process comprising:
   introducing an expression cassette that comprises a promoter and a terminator capable of functioning in *Schizosaccharomyces pombe* and a human lactate dehydrogenase gene into 3 positions of chromosome of a *Schizosaccharomyces pombe* host to obtain the transformant; and
   using a host in which a gene encoding pyruvate decarboxylase 2 is deleted or inactivated as the *Schizosaccharomyces pombe* host, or deleting or inactivating a gene encoding pyruvate decarboxylase 2 of the obtained transformant.

5. The process for producing a transformant according to claim 4, wherein the expression cassette is introduced into a region selected from a region that comprises from 10,000 bp upstream to 10,000 bp downstream of an eno101 gene locus, a region that comprises from 10,000 bp upstream to 10,000 bp downstream of a leu1 gene locus, and a region that comprises from 10,000 bp upstream to 10,000 bp downstream of a gpm1 gene locus.

6. A method for producing lactic acid, comprising cultivating the transformant as defined in claim 1, and recovering lactic acid from a culture broth.

7. The method for producing lactic acid according to claim 6, wherein a culture broth having a glucose concentration of from 1 to 50 mass % is used for cultivating the transformant.

8. The method for producing lactic acid according to claim 6, wherein the cultivating is further continued after pH of the culture broth becomes 3.5 or lower due to the lactic acid produced by the transformant.

9. The method for producing lactic acid according to claim 6, wherein the cultivating is continued without neutralizing the lactic acid produced by the transformant in the culture broth.

10. The method for producing lactic acid according to claim 6, wherein the lactic acid is separated from the culture broth without neutralizing the lactic acid produced by the transformant in the culture broth.

* * * * *

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1
ctctccagct ccatccataa g                                       21

<210> SEQ ID NO 2
<211> LENGTH: 45
<212> TYPE: DNA
<213> ORGANISM: Artificial Sequence
<220> FEATURE:
<223> OTHER INFORMATION: Synthesized

<400> SEQUENCE: 2
gacacaactt cctaccaaaa agcctttctg cccatgtttt ctgtc             45

<210> SEQ ID NO 3
<211> LENGTH: 23
<212> TYPE: DNA
<213> ORGANISM: Artificial Sequence
<220> FEATURE:
<223> OTHER INFORMATION: Synthesized

<400> SEQUENCE: 3 gcttttggt aggaagttgt gtc                                      23

<210> SEQ ID NO 4
<211> LENGTH: 43
<212> TYPE: DNA
<213> ORGANISM: Artificial Sequence
<220> FEATURE:
<223> OTHER INFORMATION: Synthesized

<400> SEQUENCE: 4
agtgggattt gtagctaagc tgtatccatt tcagccgttt gtg               43

<210> SEQ ID NO 5
<211> LENGTH: 45
<212> TYPE: DNA
<213> ORGANISM: Artificial Sequence
<220> FEATURE:
<223> OTHER INFORMATION: Synthesized

<400> SEQUENCE: 5
aagtttcgtc aatatcacaa gctgacagaa acatgggca gaaag              45

<210> SEQ ID NO 6
<211> LENGTH: 24
<212> TYPE: DNA
<213> ORGANISM: Artificial Sequence
<220> FEATURE:
<223> OTHER INFORMATION: Synthesized

<400> SEQUENCE: 6
gttccttaga aaaagcaact ttgg                                    24

<210> SEQ ID NO 7
<211> LENGTH: 20
<212> TYPE: DNA
<213> ORGANISM: Artificial Sequence

```
<220> FEATURE:
<223> OTHER INFORMATION: Synthesized

<400> SEQUENCE: 7
cataagcttg ccaccacttc                                                    20

<210> SEQ ID NO 8
<211> LENGTH: 24
<212> TYPE: DNA
<213> ORGANISM: Artificial Sequence
<220> FEATURE:
<223> OTHER INFORMATION: Synthesized

<400> SEQUENCE: 8
gaaaaagcaa ctttggtatt ctgc                                               24

<210> SEQ ID NO 9
<211> LENGTH: 21
<212> TYPE: DNA
<213> ORGANISM: Artificial Sequence
<220> FEATURE:
<223> OTHER INFORMATION: Synthesized

<400> SEQUENCE: 9
agcttagcta caaatcccac t                                                  21

<210> SEQ ID NO 10
<211> LENGTH: 23
<212> TYPE: DNA
<213> ORGANISM: Artificial Sequence
<220> FEATURE:
<223> OTHER INFORMATION: Synthesized

<400> SEQUENCE: 10
agcttgtgat attgacgaaa ctt                                                23

<210> SEQ ID NO 11
<211> LENGTH: 2811
<212> TYPE: DNA
<213> ORGANISM: Artificial Sequence
<220> FEATURE:
<223> OTHER INFORMATION: Synthesized

<400> SEQUENCE: 11
cataagcttg ccaccacttc tttccaagtg tggaagatgt tgacggtgta gtaaaaacgt         60
aaatttcctt ccaagtcttg gcttggctta atttggcctg gcctggctga tatgccacct        120
gcaaagtggt acttctaagt atgttcgcat attcttattg ccaacaaagt caagtatacg        180
aaggagtgtt cgggaaattt cctccaacga taatagattt gccgagcctt cgattagcat        240
aagagataga tgaccaatag caatagagaa taggcttctt atttgtttaa gaagctttaa        300
cggataacac acaaccaatg aacgttcccc acacattcta agaaatcgga atgagaagtc        360
tttgagtttc caatgactca taaatgcaca acaggacaga aaacatgggc agaaaggctt        420
tttggtagga agttgtgtca ttataaatag cgagatgtat tataacttcg acaaatttcc        480
cttttctttt gttataaatg ttagtgtggt acaagagaag tgaagggtta cgtagtaagc        540
ataaataata ttttgtagtc atatggattt gaacatgaaa ttagcgattc ttcagtaatt        600
ggatatttac acaaacggct gaaatggata caagcttagc tacaaatccc actggctata        660
tgtatgcatt tgtgttaaaa agtttgtat agattattta atctactcag cattctttct         720
ctaaatagga atttgttact taatggagaa aaaaatgttt cgatttacct agtgtatttg        780
```

| | |
|---|---|
| tttgtatact cacgttttaat ttcaaacatc cattctatct tgtgtaatttt ttggcatggt | 840 |
| gaaaaagata atcagcctta taatctttac aaaagtaaga aattctgtaa ataagcctta | 900 |
| atgcccttgc tttaaattaa aatggttctt tttcatgata atgtttgcac tttgtgaata | 960 |
| tattttagat agttctgtga ggtataatta agatgtttta gagacttata caattttgtc | 1020 |
| tttataaatt cttaattgat tttaccatcc cagtttaact atgcttcgtc ggcatctctg | 1080 |
| cacatgtcgt gttttcttac cgtattgtcc taccaagaac ctcttttttg cttggatcga | 1140 |
| aattaaaggt ttaaaagcaa agttatggat gctagagtat ttcaaagcta ttcagctaga | 1200 |
| gctgagggga tgaaaaatcc cattgccaag gaattgttgg ctttgatgga agaaaagcaa | 1260 |
| agcaacttgt cagtcgcggt cgatttgacg aagaaatccg aaatcttaga attggtagat | 1320 |
| aaaattggac cctatgtctg tgttatcaag acacatattg acgttgtcga ggatttcgac | 1380 |
| caggatatgg tagaaaaact ggtggcctta ggtaaaaagc atcgttttct tatctttgag | 1440 |
| gatcgcaaat tcgcagacat tggaaatacc gtcaagctac aatatgcatc tggtgtgtac | 1500 |
| aaaattgctt cttgggctca tatcacaaat tgccatacag tgccaggcga gggtattata | 1560 |
| caaggcctca aagaagttgg tttacctttg ggacgtggtc tcttgctttt ggctgaaatg | 1620 |
| tcttccaaag gctctttggc tactggttcc tacacagaga aaaccttaga atggtttgag | 1680 |
| aagcataccg attttgctt tggctttata gctggtcgtc gatttcctaa ccttcaaagc | 1740 |
| gactacataa ctatgtcccc tggtatcggc ttggatgtta aggagacgg gctgggacag | 1800 |
| caatatcgta ctcctgaaga agtgattgta aactgcggta gcgatatcat cattgttggt | 1860 |
| cgtggagtct atggagctgg tcgtaatcct gttgtcgaag ccaagagata tagagaagct | 1920 |
| ggttggaagg catatcagca aagactttct cagcattaaa aaaagactaa tgtaaaattt | 1980 |
| ttttggttgg ttattgaaaa agtcgatgcc ttgtttgcgt tgttttcct aggcgtttta | 2040 |
| tgtcagaagg catttagaat tagtatacaa gtactctttg gtaaaatttt atgtagcgac | 2100 |
| taaaatatta actattatag ataaacacct tgggaataaa aagtaatttg ctatagtaat | 2160 |
| ttattaaaca tgctcctaca acattaccac aatctttttct cttggattga cattgaataa | 2220 |
| gaaaagagtg aatttttta gacttgtaat gataactatg tacaaagcca atgaaagatg | 2280 |
| tatgtagatg aatgtaaaat accatgtaga caaacaagat aaaacttggt tataaacatt | 2340 |
| ggtgttggaa cagaataaat tagatgtcaa aaagtttcgt caatatcaca agcttgacag | 2400 |
| aaaacatggg cagaaagtcg caaagatgaa cagcatcccg cttgtagaca tgcgttaaac | 2460 |
| cacatttctt gaaaaaagtg gtgttcccac tgtatttcgt ggtattaaat aattctgacc | 2520 |
| ttttgacgat attctatttc ctcagaaaaa atgatttttt catgttgtta ctgttttcgg | 2580 |
| gaatgtgatc gttttgagaa ttagcagagc tactcgagtg ttgtggtttc accgggaagc | 2640 |
| tgtatttaca acccgagaaa gacattttc cgagtggcat ttgctatcac accgtatttg | 2700 |
| agcacaacgg caaaaataat gtgagtctcg attttgtcca agttgcctga ctcaaaaaca | 2760 |
| tatatatata cacacgtgcc atctggggca gaataccaaa gttgctttt c | 2811 |

<210> SEQ ID NO 12
<211> LENGTH: 4562
<212> TYPE: DNA
<213> ORGANISM: Artificial Sequence
<220> FEATURE:
<223> OTHER INFORMATION: Synthesized

<400> SEQUENCE: 12

| | |
|---|---|
| gtgggtgacc aaattgtcaa gcgtgagctt gccactggtg tccccattgt ctaccacttg | 60 |

```
gacaaggacg gcaagtacgt ctccaaggag ctcattgaca actagatttc ctactagatt    120
ttagtcgcct atttttaacga catatacact gttttttctac actaactcat ttctatgatg    180
ttgtataatg caatttcttt ttttgaaatc aaatcaaact acaaggtaga cgaaataata    240
gagtaattat gagggagtaa caagggagta acggggtggt ggaagaagtg agtgagttgg    300
tagtgcaagg agagagaatc gtaccaatac attaggagga agaaaaagta tcgatttagt    360
agaaagaaat agcattatcg tactgtgtga agagtttaca gtcttgctag ttattaatag    420
taatcaatta cggggtcatt agttcatagc ccatatatgg agttccgcgt tacataactt    480
acggtaaatg gcccgcctgg ctgaccgccc aacgaccccc gcccattgac gtcaataatg    540
acgtatgttc ccatagtaac gccaataggg actttccatt gacgtcaatg ggtggagtat    600
ttacggtaaa ctgcccactt ggcagtacat caagtgtatc atatgccaag tacgccccct    660
attgacgtca atgacggtaa atggcccgcc tggcattttg cccagtacat gaccttatgg    720
gactttccta cttggcagta catctacgta ttagtcatcg ctattaccat ggtgatgcgg    780
ttttggcagt acatcaatgg gcgtggatag cggtttgact cacggggatt tccaagtctc    840
caccccattg acgtcaatgg gagtttgttt tggcaccaaa atcaacggga ctttccaaaa    900
tgtcgtaaca actccgcccc attgacgcaa atgggcggta ggcgtgtacg gtgggaggtc    960
tatataagca gatttctctt tagttctttg caagaaggta gagataaaga cacttttttca   1020 aatatggatg ctagagtatt tcaaagctat tcagctagag ctgagggat gaaaaatccc    1080 attgccaagg aattgttggc tttgatggaa gaaaagcaaa gcaacttgtc agtcgcggtc    1140
gatttgacga agaaatccga aatcttagaa ttggtagata aaattggacc ctatgtctgt    1200
gttatcaaga cacatattga cgttgtcgag gatttcgacc aggatatggt agaaaaactg    1260
gtggccttag gtaaaaagca tcgttttctt atctttgagg atcgcaaatt cgcagacatt    1320
ggaaataccg tcaagctaca atatgcatct ggtgtgtaca aaattgcttc ttgggctcat    1380
atcacaaatt gccatacagt gccaggcgag ggtattatac aaggcctcaa agaagttggt    1440
ttacctttgg gacgtggtct cttgcttttg gctgaaatgt cttccaaagg ctctttggct    1500
actggttcct acacagagaa aaccttagaa tggtttgaga agcataccga ttttgcttt    1560 ggctttatag ctggtcgtcg atttcctaac cttcaaagcg actacataac tatgtcccct    1620
ggtatcggct tggatgttaa aggagacggg ctgggacagc aatatcgtac tcctgaagaa    1680
gtgattgtaa actgcggtag cgatatcatc attgttggtc gtggagtcta tggagctggt    1740
cgtaatcctg ttgtcgaagc caagagatat agagaagctg gttggaaggc atatcagcaa    1800
agactttctc agcattaaaa aaagactaat gtaaattttt tttggttggt tattgaaaaa    1860
gtcgatgcct gtttgcgtt tgttttccta ggcgttttat gtcagaaggc atttagaatt    1920
agtatacaag tactctttgg taaaattta tgtagcgact aaaatattaa ctattataga    1980
taaacacctt gggaataaaa agtaatttgc tatagtaatt tattaaacat gctcctacaa    2040
cattacctct agttattaat agtaatcaat tacggggtca ttagttcata gcccatatat    2100
ggagttccgc gttacataac ttacggtaaa tggcccgcct ggctgaccgc ccaacgaccc    2160
ccgcccattg acgtcaataa tgacgtatgt tcccatagta acgccaatag ggactttcca    2220
ttgacgtcaa tgggtggagt atttacggta aactgcccac ttggcagtac atcaagtgta    2280
tcatatgcca agtacgcccc ctattgacgt caatgacggt aaatggcccg cctggcatttt   2340 tgcccagtac atgaccttat gggactttcc tacttggcag tacatctacg tattagtcat    2400
```

```
cgctattacc atggtgatgc ggttttggca gtacatcaat gggcgtggat agcggtttga    2460
ctcacgggga tttccaagtc tccaccccat tgacgtcaat gggagtttgt tttggcacca    2520
aaatcaacgg gactttccaa aatgtcgtaa caactccgcc ccattgacgc aaatgggcgg    2580
taggcgtgta cggtgggagg tctatataag cagatttctc tttagttctt tgcaagaagg    2640
tagagataaa gacactttt  caaacatggc aactctaaag gatcagctga tttataatct    2700
tctaaaggaa gaacagaccc cccagaataa gattacagtt gttggggttg gtgctgttgg    2760
catggcctgt gccatcagta tcttaatgaa ggacttggca gatgaacttg ctcttgttga    2820
tgtcatcgaa gacaaattga agggagagat gatggatctc caacatggca gccttttcct    2880
tagaacacca aagattgtct ctggcaaaga ctataatgta actgcaaact ccaagctggt    2940
cattatcacg gctggggcac gtcagcaaga gggagaaagc cgtcttaatt tggtccagcg    3000
taacgtgaac atatttaaat tcatcattcc taatgttgta aaatacagcc cgaactgcaa    3060
gttgcttatt gtttcaaatc cagtggatat cttgacctac gtggcttgga agataagtgg    3120
ttttcccaaa aaccgtgtta ttggaagtgg ttgcaatctg gattcagccc gattccgtta    3180
cctgatgggg gaaaggctgg gagttcaccc attaagctgt catgggtggg tccttgggga    3240
acatggagat tccagtgtgc ctgtatggag tggaatgaat gttgctggtg tctctctgaa    3300
gactctgcac ccagatttag ggactgataa agataaggaa cagtggaaag aggttcacaa    3360
gcaggtggtt gagagtgctt atgaggtgat caaactcaaa ggctacacat cctgggctat    3420
tggactctct gtagcagatt tggcagagag tataatgaag aatcttaggc gggtgcaccc    3480
agtttccacc atgattaagg gtcttttacg aataaaggat gatgtcttcc ttagtgttcc    3540
ttgcattttg ggacagaatg gaatctcaga ccttgtgaag gtgactctga cttctgagga    3600
agaggcccgt tgaagaaga  gtgcagatac actttggggg atccaaaagg agctgcaatt    3660
ttaacatgtg aattcgagct cggtacccgg ggatcctcta gagtcgacct gcaggcatgc    3720
aagcttaaat aggaaagttt cttcaacagg attacagtgt agctacctac atgctgaaaa    3780
atatagcctt taaatcattt ttatattata actctgtata atagagataa gtccattttt    3840
taaaaatgtt ttccccaaac cataaaaccc tatacaagtt gttctagtaa caatacatga    3900
gaaagatgtc tatgtagctg aaaataaaat gacgtcacaa gacgatctgc ctcgcgcgtt    3960
tcggtgatga cggtgaaaac ctctgacaca tgcagctccc ggagacggtc acagcttgtc    4020
tgtaagcgga tgccgggagc agacaagccc gtcagggcgc gtcagcgggt gttggcgggt    4080
gtcgggcgc  agccatgacc cagtcacgta gcgatagcgg agtgtaatcg tttgtgaaga    4140
gtttacagtc ttgcagcaag tttctcaatg ctttagagtg cctatgtcta cgatggatgc    4200
tacgtcttcc tctgaatagt ctattaaaaa tcaacaatac ctttttgtta caaggtgttg    4260
agtgtcatta aaagacaaag tgaaatacaa ggggattatt aagaaattat agtgcggcgg    4320
agcaaagtag actagtagtc cattttctat gcacagtaga aaacaaaaag tattcaacaa    4380
aaaaaaaaaa aaacagaata cattgcaagg attagaaagc aaacaaccct tctttacaag    4440
gatgtaatga agcatatttt tattatcaaa acattgatg  atgaaattgg tatgcttttg    4500
gatactacta ttgcttttta ctctacgaca atgacatttc acattcaatt ggtttaaacc    4560
ac                                                                  4562
```

<210> SEQ ID NO 13
<211> LENGTH: 4535
<212> TYPE: DNA
<213> ORGANISM: Artificial Sequence
<220> FEATURE:
<223> OTHER INFORMATION: Synthesized

<400> SEQUENCE: 13

```
gtgcaagtac aacgagcttc tccgtatcga ggaggaactc ggttccgagg gtgtttacgc         60
tggtgcccat gctggcaagt acatcaaggc tgctaagttt taaactctga gcatacatta        120
aattttacta atgtttacaa tacatgttta tttttataga atgcaatgaa attttttatcc       180
tttttgcgtt ttggattaat ttgccaggtt gcgtgtttat ttattattag tattaaagta        240
aactgttgtt gtagtagaag tagctgatat aattgttttg tgctaatttg catccttttt        300
tttttttagat gatcatttta gttttcgttt atatagtgtt ttttttttcaa tcatcttaat      360
tttttttgga atgtgtgcat ctgctgtaaa acacagaaat ttgctagtta ttaatagtaa        420
tcaattacgg ggtcattagt tcatagccca tatatggagt tccgcgttac ataacttacg        480
gtaaatggcc cgcctggctg accgcccaac gacccccgcc cattgacgtc aataatgacg        540
tatgttccca tagtaacgcc aatagggact ttccattgac gtcaatgggt ggagtattta        600
cggtaaactg cccacttggc agtacatcaa gtgtatcata tgccaagtac gccccctatt        660
gacgtcaatg acggtaaatg gcccgcctgg cattttgccc agtacatgac cttatgggac        720
tttcctactt ggcagtacat ctacgtatta gtcatcgcta ttaccatggt gatgcggttt        780
tggcagtaca tcaatgggcg tggatagcgg tttgactcac ggggatttcc aagtctccac        840
cccattgacg tcaatgggag tttgttttgg caccaaaatc aacgggactt tccaaaatgt        900
cgtaacaact ccgccccatt gacgcaaatg ggcggtaggc gtgtacggtg ggaggtctat        960
ataagcagat ttctctttag ttctttgcaa gaaggtagag ataaagacac tttttcaaat       1020
atggatgcta gagtatttca aagctattca gctagagctg aggggatgaa aaatcccatt      1080
gccaaggaat tgttggcttt gatggaagaa aagcaaagca acttgtcagt cgcggtcgat      1140
ttgacgaaga aatccgaaat cttagaattg gtagataaaa ttggacccta tgtctgtgtt      1200
atcaagacac atattgacgt tgtcgaggat ttcgaccagg atatggtaga aaaactggtg     1260
gccttaggta aaaagcatcg ttttcttatc tttgaggatc gcaaattcgc agacattgga      1320
aataccgtca agctacaata tgcatctggt gtgtacaaaa ttgcttcttg ggctcatatc      1380
acaaattgcc atacagtgcc aggcgagggt attatacaag gcctcaaaga agttggttta     1440
cctttgggac gtggtctctt gcttttggct gaaatgtctt ccaaaggctc tttggctact      1500
ggttcctaca cagagaaaac cttagaatgg tttgagaagc ataccgattt tgctttggc      1560
tttatagctg gtcgtcgatt tcctaacctt caaagcgact acataactat gtcccctggt     1620
atcggcttgg atgttaaagg agacgggctg ggacagcaat atcgtactcc tgaagaagtg    1680
attgtaaact gcggtagcga tatcatcatt gttggtcgtg gagtctatgg agctggtcgt     1740
aatcctgttg tcgaagccaa gagatataga gaagctggtt ggaaggcata tcagcaaaga    1800
ctttctcagc attaaaaaaa gactaatgta aaatttttt ggttggttat tgaaaaagtc      1860
gatgccttgt ttgcgtttgt tttcctaggc gttttatgtc agaaggcatt tagaattagt     1920
atactacaag tactctttgg taaaatttta tgtagcgact aaaatattaa ctattataga     1980
taaacacctt gggaataaaa agtaatttgc tatagtaatt tattaaacat gctcctacaa     2040
cattacctct agttattaat agtaatcaat tacggggtca ttagttcata gcccatatat    2100
ggagttccgc gttacataac ttacggtaaa tggcccgcct ggctgaccgc ccaacgaccc    2160
ccgcccattg acgtcaataa tgacgtatgt tcccatagta acgccaatag ggactttcca    2220
```

```
ttgacgtcaa tgggtggagt atttacggta aactgcccac ttggcagtac atcaagtgta    2280
tcatatgcca agtacgcccc ctattgacgt caatgacggt aaatggcccg cctggcattt    2340
tgcccagtac atgaccttat gggactttcc tacttggcag tacatctacg tattagtcat    2400
cgctattacc atggtgatgc ggttttggca gtacatcaat gggcgtggat agcggtttga    2460
ctcacgggga tttccaagtc tccaccccat tgacgtcaat gggagtttgt tttggcacca    2520
aaatcaacgg gactttccaa aatgtcgtaa caactccgcc ccattgacgc aaatgggcgg    2580
taggcgtgta cggtgggagg tctatataag cagatttctc tttagttctt tgcaagaagg    2640
tagagataaa gacactttt caaacatggc aactctaaag gatcagctga tttataatct    2700
tctaaaggaa gaacagaccc cccagaataa gattacagtt gttggggttg gtgctgttgg    2760
catggcctgt gccatcagta tcttaatgaa ggacttggca gatgaacttg ctcttgttga    2820
tgtcatcgaa gacaaattga agggagagat gatggatctc caacatggca gccttttcct    2880
tagaacacca aagattgtct ctggcaaaga ctataatgta actgcaaact ccaagctggt    2940
cattatcacg gctgggcac gtcagcaaga gggagaaagc cgtcttaatt tggtccagcg    3000
taacgtgaac atatttaaat tcatcattcc taatgttgta aaatacagcc cgaactgcaa    3060
gttgcttatt gtttcaaatc cagtggatat cttgacctac gtggcttgga agataagtgg    3120
ttttcccaaa aaccgtgtta ttggaagtgg ttgcaatctg gattcagccc gattccgtta    3180
cctgatgggg gaaaggctgg gagttcaccc attaagctgt catgggtggg tccttgggga    3240
acatggagat tccagtgtgc ctgtatggag tggaatgaat gttgctggtg tctctctgaa    3300
gactctgcac ccagatttag ggactgataa agataaggaa cagtggaaag aggttcacaa    3360
gcaggtggtt gagagtgctt atgaggtgat caaactcaaa ggctacacat cctgggctat    3420
tggactctct gtagcagatt tggcagagag tataatgaag aatcttaggc gggtgcaccc    3480
agtttccacc atgattaagg gtctttacgg aataaaggat gatgtcttcc ttagtgttcc    3540 ttgcatttg ggacagaatg gaatctcaga ccttgtgaag gtgactctga cttctgagga    3600
agaggcccgt ttgaagaaga gtgcagatac actttgggg atccaaaagg agctgcaatt    3660
ttaacggtac ccggggatcc tctagagtcg acctgcaggc atgcaagctt aaataggaaa    3720
gtttcttcaa caggattaca gtgtagctac ctacatgctg aaaaatatag cctttaaatc    3780 attttatat tataactctg tataatagag ataagtccat tttttaaaaa tgttttcccc    3840
aaaccataaa accctataca agttgttcta gtaacaatac atgagaaaga tgtctatgta    3900
gctgaaaata aaatgacgtc acaagacgat ctgcctcgcg cgtttcggtg atgacggtga    3960
aaacctctga cacatgcagc tcccggagac ggtcacagct tgtctgtaag cggatgccgg    4020
gagcagacaa gcccgtcagg gcgcgtcagc gggtgttggc gggtgtcggg gcgcagccat    4080
gacccagtca cgtagcgata gcggagtgta atcgtttctg taaaacacag aaatttgtct    4140
ttgacctagt acatattttt atgtgtagcc aaaatttttg atacctttg ctctttatca    4200 gtcactttac tactactaac actggaaaat gttctattcc tcagcatctt acctactagt    4260
atttataata ttcatcaacg tagaatgaaa ataacaatat tattaacata attcatctac    4320
attacaatag taaatattg aaccagaaaa gccaaaaaaa aaaagcata tagaaaagga    4380 aatcatttgt acagaaaagt catgaacgaa aaacatgtca taaattaagg accgtatagg    4440
ctttatgcat ttaagtaaaa aaaaaaaaaa aagaacagc attaaagtgg tgaaacaaat    4500
taaacaacaa gggaaatcaa agccgtttaa accac                              4535
```

<210> SEQ ID NO 14
<211> LENGTH: 3277
<212> TYPE: DNA
<213> ORGANISM: Artificial Sequence
<220> FEATURE:
<223> OTHER INFORMATION: Synthesized

<400> SEQUENCE: 14

| | | | | | |
|---|---|---|---|---|---|
| gtgtgtactt | tgaaagtcta | gctttacagc | ttggcattgt | tcatacaaac gtcttcagca | 60 |
| tatctttcca | cacttgctct | gtacacgtat | tctttccctc | ttatcattcc tgttttctt | 120 |
| ttttaataaa | ccaacatgcc | tgtaagtagt | tttatcttta | gaaatctgtg catcatggat | 180 |
| cctaactatg | tcttttagac | ggttcaaact | ccctctcagc | gtcgtgcaaa cacacagttt | 240 |
| cagaagaaca | ttactcgtcg | tgtaaaaaca | aattcaaaag | aacgttatgt tgccaaacat | 300 |
| cctcctacca | agattcctcg | taacattgcc | agtaagtaag | aattgatcct attgttagca | 360 |
| actttggctt | gtgtttcata | ctgacaatgc | atcttagtgt | tttttattct tctcatgtca | 420 |
| ggaggaatta | ttttgggaat | acttagattt | cttttgacgt | tttttcta agaacatgtg | 480 |
| attggagcaa | ttttaaaacc | tatttgcacc | gatattgtgt | attatactcc gagaaaagt | 540 |
| atactagttt | tgaataataa | agcttgtgat | attgacgaaa | cttttgaca tctaatttat | 600 |
| tctgttccaa | caccaatgtt | tataaccaag | ttttatcttg | tttgtctaca tggtatttta | 660 |
| cattcatcta | catacatctt | tcattggctt | tgtacatagt | tatcattaca agtctaaaaa | 720 |
| aattcactct | tttcttattc | aatgtcaatc | caagagaaaa | gattgtggta atgttgtagg | 780 |
| agcatgttta | ataaattact | atagcaaatt | acttttatt | cccaaggtgt ttatctataa | 840 |
| tagttaatat | tttagtcgct | acataaaatt | ttaccaaaga | gtacttgtat actaattcta | 900 |
| aatgccttct | gacataaaac | gcctaggaaa | acaaacgcaa | acaaggcatc gactttttca | 960 |
| ataaccaacc | aaaaaaattt | tacattagtc | ttttttttaat | gctgagaaag tctttgctga | 1020 |
| tatgccttcc | aaccagcttc | tctatatctc | ttggcttcga | caacaggatt acgaccagct | 1080 |
| ccatagactc | cacgaccaac | aatgatgata | tcgctaccgc | agtttacaat cacttcttca | 1140 |
| ggagtacgat | attgctgtcc | cagcccgtct | cctttaacat | ccaagccgat accaggggac | 1200 |
| atagttatgt | agtcgctttg | aaggttagga | aatcgacgac | cagctataaa gccaaagcaa | 1260 |
| aaatcggtat | gcttctcaaa | ccattctaag | gttttctctg | tgtaggaacc agtagccaaa | 1320 |
| gagcctttgg | aagacatttc | agccaaaagc | aagagaccac | gtcccaaagg taaaccaact | 1380 |
| tctttgaggc | cttgtataat | accctcgcct | ggcactgtat | ggcaatttgt gatatgagcc | 1440 |
| caagaagcaa | ttttgtacac | accagatgca | tattgtagct | tgacggtatt tccaatgtct | 1500 |
| gcgaatttgc | gatcctcaaa | gataagaaaa | cgatgctttt | tacctaaggc caccagtttt | 1560 |
| tctaccatat | cctggtcgaa | atcctcgaca | acgtcaatat | gtgtcttgat aacacagaca | 1620 |
| tagggtccaa | ttttatctac | caattctaag | atttcggatt | tcttcgtcaa atcgaccgcg | 1680 |
| actgacaagt | tgctttgctt | tcttccatc | aaagccaaca | attccttggc aatgggattt | 1740 |
| ttcatcccct | cagctctagc | tgaatagctt | tgaaatactc | tagcatccat aactttgctt | 1800 |
| ttaaaccttt | aatttcgatc | caagcaaaaa | agaggttctt | ggtaggacaa tacggtaaga | 1860 |
| aaacacgaca | tgtgcagaga | tgccgacgaa | gcatagttaa | actgggatgg taaaatcaat | 1920 |
| taagaattta | taaagacaaa | attgtataag | tctctaaaac | atcttaatta tacctcacag | 1980 |
| aactatctaa | aatatattca | caaagtgcaa | acattatcat | gaaaagaac cattttaatt | 2040 |
| taaagcaagg | gcattaaggc | ttatttacag | aatttcttac | ttttgtaaag attataaggc | 2100 |

```
tgattatctt tttcaccatg ccaaaaatta cacaagatag aatggatgtt tgaaattaaa    2160
cgtgagtata caaacaaata cactaggtaa atcgaaacat tttttctcc attaagtaac     2220 aaattcctat ttagagaaag aatgctgagt agattaaata atctatacaa actttttaa     2280 cacaaatgca tacatatagc cagtgggatt tgtagctaag cttcaggagt tttatccatt    2340
taatgtatgg aatcaaaatt taaagcttct gtcaaagttt aacaatattt cttttggttt    2400
aaatcaaatc ttccatgcga ttaagaagat agatgctgaa caaagaagc acatggataa     2460 ccacaaaagc agtttgctca tgggtacaac catgaatttt tttttcgaca atgattcaaa    2520
gaccagtata tccaatacgc atcctagaat ctagtcaaag aagaacctaa agtagagatg    2580
caaatgcgct aaaaagagtg gatataaatt caatatcatt tataaaacaa cttcttccat    2640
taaaaattcc ttgggcaaaa caaagttcc aatcataaaa agttaataag ttctgagttg      2700
tgtcaaatct gacatggcat tcctcaataa tgacactcac tcattatgta agcatcgaaa    2760
acatattaaa atctatacaa gctgttttgt cattacggtc tggcatcaac tttttagag     2820 gcggtacgaa gatgattttg cacacggata accaattctt catgagatcc gctagttta     2880 agtgaatttt ttttacaata ctcaattaac tgtttttttg accattgact aggaggactt    2940
tgagaaatgg aggatgaagc tgtctccctg gaattgtctg tgataggact aactacaacc    3000
gccagggaag aagcagcaat aattgcagca aacgataaag ttaagacatt agctattttc    3060
atcgaagatg aaatacaaat gagtaaaaag aacccaaaaa tgaaaactgt tattaaaaag    3120
gagattttga aaatttaaag gttgaggtaa agaacggttg tagaagacga gcatctagag    3180
gaagacgccc ccaactgtgg ccaacgtttt tcattaccca aattcatctg acattgatta    3240
tgatacattg aaggtgtgct tacatctttc tagtcat                             3277
```